US007968562B2

(12) United States Patent
Skwierczynski et al.

(10) Patent No.: US 7,968,562 B2
(45) Date of Patent: Jun. 28, 2011

(54) PHARMACEUTICAL FORMULATIONS COMPRISING AN IMMUNE RESPONSE MODIFIER

(75) Inventors: Raymond D. Skwierczynski, Oakdale, MN (US); Terri F. Busch, St. Paul, MN (US); Amy L. Gust-Heiting, Hudson, WI (US); Mary Fretland, Eagan, MN (US); Matthew T. Scholz, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/172,712

(22) Filed: Jul. 14, 2008

(65) Prior Publication Data
US 2008/0275077 A1 Nov. 6, 2008

Related U.S. Application Data

(63) Continuation of application No. 10/306,019, filed on Nov. 27, 2002, now abandoned.

(60) Provisional application No. 60/340,605, filed on Nov. 29, 2001, provisional application No. 60/378,452, filed on May 6, 2002.

(51) Int. Cl.
| | |
|---|---|
| A01N 43/42 | (2006.01) |
| A01N 43/50 | (2006.01) |
| A61K 31/44 | (2006.01) |
| A61K 31/415 | (2006.01) |
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |

(52) U.S. Cl. ................ 514/292; 514/397; 546/81
(58) Field of Classification Search .......... 514/292, 514/397; 546/81
See application file for complete search history.

(56) References Cited

U.S. PATENT DOCUMENTS

| | | |
|---|---|---|
| 3,314,941 A | 4/1967 | Littell et al. |
| 4,595,586 A | 6/1986 | Flom |
| 4,689,338 A | 8/1987 | Gerster |
| 4,698,348 A | 10/1987 | Gerster |
| 4,722,941 A | 2/1988 | Eckert et al. |
| 4,800,076 A | 1/1989 | Bhat et al. |
| 4,929,624 A | 5/1990 | Gerster et al. |
| 4,973,468 A | 11/1990 | Chiang et al. |
| 4,988,815 A | 1/1991 | Andre et al. |
| 4,996,193 A | 2/1991 | Hewitt et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,728,732 A * | 3/1998 | Corey et al. ................ 514/544 |
| 5,741,908 A | 4/1998 | Gerster et al. |
| 5,756,747 A | 5/1998 | Gerster |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,248,763 B1 * | 6/2001 | Scivoletto ................ 514/356 |
| 6,331,539 B1 | 12/2001 | Crooks et al. |
| 6,376,669 B1 | 4/2002 | Rice et al. |
| 6,451,810 B1 | 9/2002 | Coleman et al. |
| 6,486,168 B1 | 11/2002 | Skwierczynski et al. |
| 6,582,710 B2 * | 6/2003 | Deckers et al. ............ 424/401 |
| 2002/0055517 A1 | 5/2002 | Smith |
| 2002/0058674 A1 | 5/2002 | Hedenstrom et al. |

FOREIGN PATENT DOCUMENTS

| | | |
|---|---|---|
| EP | 0 394 026 | 10/1990 |
| EP | 1 104 764 | 6/2001 |
| JP | 9-208584 | 8/1997 |
| JP | 9-255926 | 3/1999 |
| JP | 11-222432 | 8/1999 |
| JP | 2000-247884 | 9/2000 |
| JP | 2001-64165 | 3/2001 |
| WO | WO 98/36747 | 8/1998 |
| WO | WO 99/29693 | 6/1999 |
| WO | WO 9929693 | * 6/1999 |
| WO | WO 00/25732 | 5/2000 |

(Continued)

OTHER PUBLICATIONS

Attwood, D., Florence, A. T. *Surfactant Systems: Their Chemistry, Pharmacy, and Biology*, New York: Chapman & Hall, 471-473, 1983.

(Continued)

*Primary Examiner* — Sreeni Padmanabhan
*Assistant Examiner* — Kendra D Carter

(57) ABSTRACT

Pharmaceutical formulations comprising an immune response modifier (IRM) chosen from imidazoquinoline amines, imidazotetrahydroquinoline amines, imidazopyridine amines, 6,7-fused cycloalkylimidazopyridine amines, 1,2-bridged imidazoquinoline amines, thiazolo-quinolineamines, oxazolo-quinolinamines, thiazolo-pyridinamines, oxazolo-pyridinamines, imidazonaphthyridine amines, tetrahydroimidazonaphthyridine amines, and thiazolonaphthyridine amines; a fatty acid; and a hydrophobic, aprotic component miscible with the fatty acid are useful for the treatment of dermal associated conditions. Novel topical formulations are provided. In one embodiment, the topical formulations are advantageous for treatment of actinic keratosis, postsurgical scars, basal cell carcinoma, atopic dermatitis, and warts.

12 Claims, No Drawings

FOREIGN PATENT DOCUMENTS

| WO | WO 00/40228 | 7/2000 |
| WO | WO 00/47719 | 8/2000 |
| WO | WO 00/76518 | 12/2000 |
| WO | WO 01/74343 | 10/2001 |
| WO | WO 02/36592 | 5/2002 |
| WO | WO 02/46188 | 6/2002 |
| WO | WO 02/46189 | 6/2002 |
| WO | WO 02/46190 | 6/2002 |
| WO | WO 02/46191 | 6/2002 |
| WO | WO 02/46192 | 6/2002 |
| WO | WO 02/46193 | 6/2002 |
| WO | WO 02/46194 | 6/2002 |
| WO | WO 02/46749 | 6/2002 |
| WO | WO 02/102377 | 12/2002 |

OTHER PUBLICATIONS

Chollet J L et al: "Development of a Topically Active Imiquimod Formulation" Pharmaceutical Development and Technology, New York, NY, US, vol. 4, No. 1, Jan. 1999, pp. 35-43.

Miller, et al., "Imiquimod Applied Topically: a novel immune response modifier and new class of drug", *International Journal of Immunopharmacology*, 21, pp. 1-14 (1999).

Wozniak, et al, "The Amination of 3-nitro-1, 5-naphthyridines by Liquid Ammonia/Potassium Permanganate[1,2], A New and Convenient Amination Method.", *Journal of the Royal Netherlands Chemical Society*, 102, pp. 511-513, Dec. 12, 1983.

Brennan, et al, "Automated Bioassay of Interferons in Micro-test Plates", *Biotechniques*, Jun./Jul. 78, 1983.

Testerman, et al., "Cytokine Induction by the Immunomodulators Imiquimod and S-27609", *Journal of Leukocyte Biology*, vol. 58, pp. 365-372, Sep. 1995.

Bachman, et al, "Synthesis of Substituted Quinolylamines. Derivatives of 4-Amino-7-Chloroquinoline", *J. Org. Chem*, 15, pp. 1278-1284 (1950).

Jain, et al, "Chemical and Pharmacological Investigations of Some ω-Substituted Alkylamino-3-aminopyridines", *J. Med. Chem*., 11, pp. 87-92 (1968).

Baranov, et al., *Chem. Abs*. 85, 94371, (1976).

Berényi, et al, "Ring Transformation of Condensed Dihydro-astriazines", *J. Heterocyclic Chem*., 18, pp. 1537-1540 (1981).

Merck Index 10th edition, Windholtz et al Eds., Merck & Co., Rahway, NJ, 1983 abstracts 1020. 7135.

* cited by examiner

PHARMACEUTICAL FORMULATIONS COMPRISING AN IMMUNE RESPONSE MODIFIER

CROSS REFERENCE TO RELATED APPLICATIONS

This application is a continuation of U.S. application Ser. No. 10/306,019, filed Nov. 27, 2002 now abandoned, which claims priority to Provisional Patent Application Ser. No. 60/340,605, filed Nov. 29, 2001 and Provisional Patent Application Ser. No. 60/378,452, filed May 6, 2002, the disclosures of which are incorporated by reference herein in their entirety.

FIELD OF THE INVENTION

The present invention is directed to pharmaceutical formulations comprising at least one immune response modifier chosen from imidazoquinoline amines, imidazopyridine amines, 6,7-fused cycloalkylimidazopyridine amines, 1,2-bridged imidazoquinoline amines, thiazoloquinoline amines, oxazoloquinoline amines, thiazolopyridine amines, oxazolopyridine amines, imidazonaphthyridine amines, imidazotetrahydronaphthyridine amines, and thiazolonaphthyridine amines. Embodiments of the present invention are directed to topical formulations for application to the skin of a mammal. Other embodiments of the present invention are directed to methods for treating dermal diseases.

BACKGROUND

Many imidazoquinoline amine, imidazopyridine amine, 6,7-fused cycloalkylimidazopyridine amine, 1,2-bridged imidazoquinoline amine, thiazoloquinoline amine, oxazoloquinoline amine, thiazolopyridine amine, oxazolopyridine amine, imidazonaphthyridine amine, imidazotetrahydronaphthyridine amine, and thiazolonaphthyridine amine compounds have demonstrated potent immunostimulating, antiviral and antitumor (including anticancer) activity, and have also been shown to be useful as vaccine adjuvants. These compounds are hereinafter collectively referred to as "IRM" (immune response modifier) compounds. One of these IRM compounds, known as imiquimod, has been commercialized in a topical formulation, Aldara™, for the treatment of anogenital warts associated with human papillomavirus.

The mechanism for the antiviral and antitumor activity of these IRM compounds is thought to be due in substantial part to enhancement of the immune response by induction of various important cytokines (e.g., interferons, interleukins, tumor necrosis factor, etc.). Such compounds have been shown to stimulate a rapid release of certain monocyte/macrophage-derived cytokines and are also capable of stimulating B cells to secrete antibodies which play an important role in these IRM compounds' antiviral and antitumor activities. One of the predominant immunostimulating responses to these compounds is the induction of interferon (IFN)-α production, which is believed to be very important in the acute antiviral and antitumor activities seen. Moreover, up regulation of other cytokines such as, for example, tumor necrosis factor (TNF), Interleukin-1 (IL-1) and IL-6 also have potentially beneficial activities and are believed to contribute to the antiviral and antitumor properties of these compounds.

Although some of the beneficial effects of IRMs are known, the ability to provide therapeutic benefit via topical application of an IRM compound for treatment of a particular condition at a particular location may be hindered by a variety of factors. These factors include irritation of the skin to which the formulation is applied, formulation wash away, insolubility and/or degradation of the IRM compound in the formulation, physical instability of the formulation (e.g., separation of components, thickening, precipitation/agglomerization of active ingredient, and the like), poor permeation, and undesired systemic delivery of the topically applied IRM compound. Accordingly, there is a continuing need for new methods and formulations to provide the greatest therapeutic benefit from this class of compounds.

SUMMARY OF THE INVENTION

At several locations throughout the specification, guidance is provided through lists of examples. In each instance, the recited list serves only as a representative group; it is not meant that the list is exclusive.

In one aspect, the present invention is directed to a pharmaceutical formulation comprising an immune response modifier selected from imidazoquinoline amines, imidazotetrahydroquinoline amines, imidazopyridine amines, 6,7-fused cycloalkylimidazopyridine amines, 1,2-bridged imidazoquinoline amines, thiazoloquinoline amines, oxazoloquinoline amines, thiazolopyridine amines, oxazolopyridine amines, imidazonaphthyridine amines, imidazotetrahydronaphthyridine amines, and thiazolonaphthyridine amines; a fatty acid; a hydrophobic, aprotic component miscible with the fatty acid and comprising a hydrocarbyl group of 7 or more carbon atoms; and a hydrophilic viscosity enhancing agent selected from cellulose ethers and carbomers.

In one embodiment, the pharmaceutical formulation comprises an immune response modifier selected from imidazonaphthyridine amines, imidazotetrahydronaphthyridine amines, and thiazolonaphthyridine amines; a fatty acid; and a hydrophobic, aprotic component miscible with the fatty acid and comprising a hydrocarbyl group of 7 or more carbon atoms.

The formulation can further comprise one or more of a preservative system, an emulsifier, and water.

In another aspect, the present invention is directed to a method of treatment of a dermal associated condition comprising applying to skin a topical formulation comprising an immune response modifier selected from imidazoquinoline amines, imidazotetrahydroquinoline amines, imidazopyridine amines, 6,7-fused cycloalkylimidazopyridine amines, 1,2-bridged imidazoquinoline amines, thiazoloquinoline amines, oxazoloquinoline amines, thiazolopyridine amines, oxazolopyridine amines, imidazonaphthyridine amines, imidazotetrahydronaphthyridine amines, and thiazolonaphthyridine amines; a fatty acid; a hydrophobic, aprotic component miscible with the fatty acid and comprising a hydrocarbyl group of 7 or more carbon atoms; and a hydrophilic viscosity enhancing agent selected from cellulose ethers and carbomers.

In one embodiment, the method of treatment of a dermal associated condition comprises applying to skin a formulation comprising an immune response modifier selected from imidazonaphthyridine amines, imidazotetrahydronaphthyridine amines, and thiazolonaphthyridine amines; a fatty acid; and a hydrophobic, aprotic component miscible with the fatty acid and comprising a hydrocarbyl group of 7 or more carbon atoms.

In other embodiments, the method of treatment of a dermal associated condition comprises applying to skin a formulation comprising an immune response modifier selected from imidazonaphthyridine amines, imidazotetrahydronaphthyridine amines, and thiazolonaphthyridine amines; a fatty acid; a hydrophobic, aprotic component miscible with the fatty acid and comprising a hydrocarbyl group of 7 or more carbon atoms; and further comprising one or more of a preservative system, an emulsifier, and water.

In one embodiment, the dermal associated condition is selected from actinic keratosis, postsurgical scars, basal cell carcinoma, atopic dermatitis, and warts.

In another aspect, the present invention is directed to a method for delivering an immune response modifier to a dermal surface, the method comprising the steps of selecting a formulation comprising a compound selected from imidazoquinoline amines, imidazotetrahydroquinoline amines, imidazopyridine amines, 6,7-fused cycloalkylimidazopyridine amines, 1,2-bridged imidazoquinoline amines, thiazoloquinoline amines, oxazolo-quinoline amines, thiazolopyridine amines, oxazolopyridine amines, imidazonaphthyridine amines, imidazotetrahydronaphthyridine amines, and thiazolonaphthyridine amines; a fatty acid; a hydrophobic, aprotic component miscible with the fatty acid and comprising a hydrocarbyl group of 7 or more carbon atoms; and a hydrophilic viscosity enhancing agent selected from cellulose ethers and carbomers; and applying the selected formulation to the dermal surface for a time sufficient to allow the formulation to deliver the IRM to the dermal surface.

In one embodiment, the selected formulation comprises an immune response modifier selected from imidazonaphthyridine amines, imidazotetrahydronaphthyridine amines, and thiazolonaphthyridine amines; a fatty acid; and a hydrophobic, aprotic component miscible with the fatty acid and comprising a hydrocarbyl group of 7 or more carbon atoms.

Unless otherwise indicated, all numbers expressing quantities, ratios, and numerical properties of ingredients, reaction conditions, and so forth used in the specification and claims are to be understood as being modified in all instances by the term "about".

As used herein, "a" or "an" or "the" are used interchangeably with "at least one", to mean "one or more" of the element being modified.

DETAILED DESCRIPTION

In one aspect, the present invention is directed to a formulation comprising an immune response modifier compound selected from imidazoquinoline amines, imidazotetrahydroquinoline amines, imidazopyridine amines, 6,7-fused cycloalkylimidazopyridine amines, 1,2-bridged imidazoquinoline amines, thiazoloquinoline amines, oxazoloquinoline amines, thiazolopyridine amines, oxazolopyridine amines, imidazonaphthyridine amines, imidazotetrahydronaphthyridine amines, and thiazolonaphthyridine amines; a fatty acid; a hydrophobic, aprotic component miscible with the fatty acid and comprising a hydrocarbyl group of 7 or more carbon atoms, and a hydrophilic viscosity enhancing agent selected from cellulose ethers and carbomers.

These immune response modifier compounds, methods of making them, methods of using them and compositions containing them are disclosed in U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; and 6,451,810; European Patent 0 394 026; US Publication 2002/0055517; and PCT Publications WO 00/47719; WO 00/76518; WO 01/74343; WO 02/46188; WO 02/46189; WO 02/46190; WO 02/46191; WO 02/46192; WO 02/46193; WO 02/46194; and WO 02/46749 the disclosures of which are incorporated by reference herein.

As noted above, many of the IRM compounds useful in the present invention have demonstrated significant immunomodulating activity. In certain embodiments of the present invention, the IRM compound can be chosen from imidazoquinoline amines, for example, 1H-imidazo[4,5-c]quinolin-4-amines defined by one of Formulas I-V below:

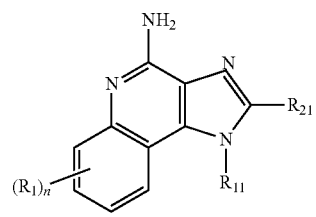

I wherein $R_{11}$ is chosen from alkyl of one to ten carbon atoms, hydroxyalkyl of one to six carbon atoms, acyloxyalkyl wherein the acyloxy moiety is alkanoyloxy of two to four carbon atoms or benzoyloxy, and the alkyl moiety contains one to six carbon atoms, benzyl, (phenyl)ethyl and phenyl, said benzyl, (phenyl)ethyl or phenyl substituent being optionally substituted on the benzene ring by one or two moieties independently chosen from alkyl of one to four carbon atoms, alkoxy of one to four carbon atoms and halogen, with the proviso that if said benzene ring is substituted by two of said moieties, then said moieties together contain no more than six carbon atoms;

$R_{21}$ is chosen from hydrogen, alkyl of one to eight carbon atoms, benzyl, (phenyl)ethyl and phenyl, the benzyl, (phenyl)ethyl or phenyl substituent being optionally substituted on the benzene ring by one or two moieties independently chosen from alkyl of one to four carbon atoms, alkoxy of one to four carbon atoms and halogen, with the proviso that when the benzene ring is substituted by two of said moieties, then the moieties together contain no more than six carbon atoms; and each $R_1$ is independently chosen from alkoxy of one to four carbon atoms, halogen, and alkyl of one to four carbon atoms, and n is an integer from 0 to 2, with the proviso that if n is 2, then said $R_1$ groups together contain no more than six carbon atoms;

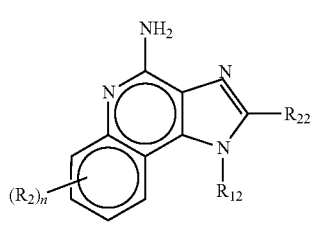

II wherein $R_{12}$ is chosen from straight chain or branched chain alkenyl containing two to ten carbon atoms and substituted straight chain or branched chain alkenyl containing two to ten carbon atoms, wherein the substituent is chosen from straight chain or branched chain alkyl containing one to four carbon atoms and cycloalkyl containing three to six carbon atoms; and cycloalkyl containing three to six carbon atoms substituted by straight chain or branched chain alkyl containing one to four carbon atoms; and $R_{22}$ is chosen from hydrogen, straight chain or branched chain alkyl containing one to eight carbon atoms, benzyl, (phenyl)ethyl and phenyl, the benzyl, (phenyl)ethyl or phenyl substituent being optionally substituted on the benzene ring by one or two moieties independently chosen from straight chain or branched chain alkyl containing one to four carbon atoms, straight chain or branched chain alkoxy containing one to four carbon atoms, and halogen, with the proviso that when the benzene ring is substituted by two such moieties, then the moieties together contain no more than six carbon atoms; and each $R_2$ is independently chosen from straight chain or branched chain alkoxy containing one to four carbon atoms, halogen, and straight chain or branched chain alkyl containing one to four carbon atoms, and n is an integer from zero to 2, with the proviso that if n is 2, then said $R_2$ groups together contain no more than six carbon atoms;

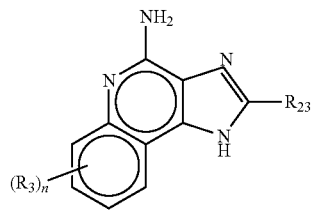

III wherein $R_{23}$ is chosen from hydrogen, straight chain or branched chain alkyl of one to eight carbon atoms, benzyl, (phenyl)ethyl and phenyl, the benzyl, (phenyl)ethyl or phenyl substituent being optionally substituted on the benzene ring by one or two moieties independently chosen from straight chain or branched chain alkyl of one to four carbon atoms, straight chain or branched chain alkoxy of one to four carbon atoms, and halogen, with the proviso that when the benzene ring is substituted by two such moieties, then the moieties together contain no more than six carbon atoms; and each $R_3$ is independently chosen from straight chain or branched chain alkoxy of one to four carbon atoms, halogen, and straight chain or branched chain alkyl of one to four carbon atoms, and n is an integer from zero to 2, with the proviso that if n is 2, then said $R_3$ groups together contain no more than six carbon atoms;

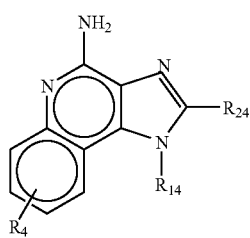

IV wherein $R_{14}$ is —CHR$_x$R$_y$ wherein R$_y$ is hydrogen or a carbon-carbon bond, with the proviso that when R$_y$ is hydrogen R$_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, or 2-, 3-, or 4-pyridyl, and with the further proviso that when R$_y$ is a carbon-carbon bond R$_y$ and R$_x$ together form a tetrahydrofuranyl group optionally substituted with one or more substituents independently chosen from hydroxy and hydroxyalkyl of one to four carbon atoms;

$R_{24}$ is chosen from hydrogen, alkyl of one to four carbon atoms, phenyl, and substituted phenyl wherein the substituent is chosen from alkyl of one to four carbon atoms, alkoxy of one to four carbon atoms, and halogen; and $R_4$ is chosen from hydrogen, straight chain or branched chain alkoxy containing one to four carbon atoms, halogen, and straight chain or branched chain alkyl containing one to four carbon atoms;

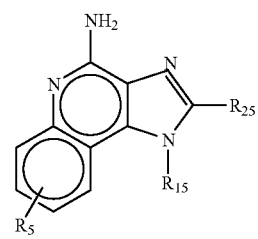

V wherein $R_{15}$ is chosen from: hydrogen; straight chain or branched chain alkyl containing one to ten carbon atoms and substituted straight chain or branched chain alkyl containing one to ten carbon atoms, wherein the substituent is chosen from cycloalkyl containing three to six carbon atoms and cycloalkyl containing three to six carbon atoms substituted by straight chain or branched chain alkyl containing one to four carbon atoms; straight chain or branched chain alkenyl containing two to ten carbon atoms and substituted straight chain or branched chain alkenyl containing two to ten carbon atoms, wherein the substituent is chosen from cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms; benzyl; (phenyl)ethyl; and phenyl; said benzyl, (phenyl)ethyl or phenyl substituent being optionally substituted on the benzene ring by one or two moieties independently chosen from alkyl of one to four carbon atoms, alkoxy of one to four carbon atoms, and halogen, with the proviso that when said benzene ring is substituted by two of said moieties, then the moieties together contain no more than six carbon atoms;

$R_{25}$ is

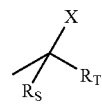

wherein $R_S$ and $R_T$ are independently chosen from hydrogen, alkyl of one to four carbon atoms, phenyl, and substituted phenyl wherein the substituent is chosen from alkyl of one to four carbon atoms, alkoxy of one to four carbon atoms, and halogen;

X is chosen from alkoxy containing one to four carbon atoms, alkoxyalkyl wherein the alkoxy moiety contains one to four carbon atoms and the alkyl moiety contains one to four carbon atoms, hydroxyalkyl of one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, chloro, hydroxy, 1-morpholino, 1-pyrrolidino, alkylthio of one to four carbon atoms; and $R_5$ is chosen from hydrogen, straight chain or branched chain alkoxy containing one to four carbon atoms, halogen, and straight chain or branched chain alkyl containing one to four carbon atoms;

and a pharmaceutically acceptable salt of any of the foregoing.

The IRM compound can also be chosen from 6,7 fused cycloalkylimidazopyridine amines defined by Formula VI below:

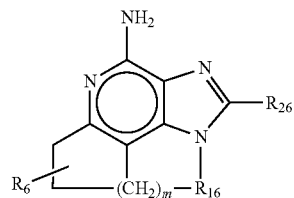

VI wherein m is 1, 2, or 3;

$R_{16}$ is chosen from hydrogen; cyclic alkyl of three, four, or five carbon atoms; straight chain or branched chain alkyl containing one to ten carbon atoms and substituted straight chain or branched chain alkyl containing one to ten carbon atoms, wherein the substituent is chosen from cycloalkyl containing three to six carbon atoms and cycloalkyl containing three to six carbon atoms substituted by straight chain or branched chain alkyl containing one to four carbon atoms; fluoro- or chloroalkyl containing from one to ten carbon atoms and one or more fluorine or chlorine atoms; straight chain or branched chain alkenyl containing two to ten carbon atoms and substituted straight chain or branched chain alkenyl containing two to ten carbon atoms, wherein the substituent is chosen from cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently chosen from alkyl of one to four carbon atoms, alkoxy of one to four carbon atoms, and halogen, with the proviso that when said benzene ring is substituted by two of said moieties, then the moieties together contain no more than six carbon atoms;

and —$CHR_xR_y$ wherein $R_y$ is hydrogen or a carbon-carbon bond, with the proviso that when $R_y$ is hydrogen $R_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, or 2-, 3-, or 4-pyridyl, and with the further proviso that when $R_y$ is a carbon-carbon bond $R_y$ and $R_x$ together form a tetrahydrofuranyl group optionally substituted with one or more substituents independently chosen from hydroxy and hydroxyalkyl of one to four carbon atoms, $R_{26}$ is chosen from hydrogen, straight chain or branched chain alkyl containing one to eight carbon atoms, straight chain or branched chain hydroxyalkyl containing one to six carbon atoms, morpholinoalkyl, benzyl, (phenyl)ethyl and phenyl, the benzyl, (phenyl)ethyl or phenyl substituent being optionally substituted on the benzene ring by a moiety chosen from methyl, methoxy, and halogen; and —$C(R_S)(R_T)(X)$ wherein $R_S$ and $R_T$ are independently chosen from hydrogen, alkyl of one to four carbon atoms, phenyl, and substituted phenyl wherein the substituent is chosen from alkyl of one to four carbon atoms, alkoxy of one to four carbon atoms, and halogen;

X is chosen from alkoxy containing one to four carbon atoms, alkoxyalkyl wherein the alkoxy moiety contains one to four carbon atoms and the alkyl moiety contains one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, alkylthio of one to four carbon atoms, and morpholinoalkyl wherein the alkyl moiety contains one to four carbon atoms, and $R_6$ is chosen from hydrogen, fluoro, chloro, straight chain or branched chain alkyl containing one to four carbon atoms, and straight chain or branched chain fluoro- or chloroalkyl containing one to four carbon atoms and at least one fluorine or chlorine atom;

and pharmaceutically acceptable salts thereof.

In other embodiments of the present invention, the IRM compound can be chosen from imidazopyridine amines defined by Formula VII below:

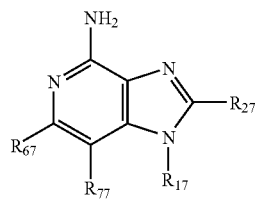

VII wherein $R_{17}$ is chosen from hydrogen; —$CH_2R_W$ wherein $R_W$ is chosen from straight chain, branched chain, or cyclic alkyl containing one to ten carbon atoms, straight chain or branched chain alkenyl containing two to ten carbon atoms, straight chain or branched chain hydroxyalkyl containing one to six carbon atoms, alkoxyalkyl wherein the alkoxy moiety contains one to four carbon atoms and the alkyl moiety contains one to six carbon atoms, and phenylethyl; and —$CH═CR_ZR_Z$ wherein each $R_Z$ is independently straight chain, branched chain, or cyclic alkyl of one to six carbon atoms;

R$_{27}$ is chosen from hydrogen; straight chain or branched chain alkyl containing one to eight carbon atoms; straight chain or branched chain hydroxyalkyl containing one to six carbon atoms; alkoxyalkyl wherein the alkoxy moiety contains one to four carbon atoms and the alkyl moiety contains one to six carbon atoms; benzyl, (phenyl)ethyl and phenyl, the benzyl, (phenyl)ethyl and phenyl being optionally substituted on the benzene ring by a moiety chosen from methyl, methoxy, and halogen; and morpholinoalkyl wherein the alkyl moiety contains one to four carbon atoms;

R$_{67}$ and R$_{77}$ are independently chosen from hydrogen and alkyl of one to five carbon atoms, with the proviso that R$_{67}$ and R$_{77}$ taken together contain no more than six carbon atoms, and with the further proviso that when R$_{77}$ is hydrogen then R$_{67}$ is other than hydrogen and R$_{27}$ is other than hydrogen or morpholinoalkyl, and with the further proviso that when R$_{67}$ is hydrogen then R$_{77}$ and R$_{27}$ are other than hydrogen;

and pharmaceutically acceptable salts thereof.

In yet another embodiment of the present invention, the IRM compound can be chosen from 1,2-bridged imidazoquinoline amines defined by Formula VIII below:

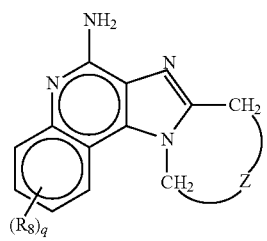

VIII wherein

Z is chosen from:

—(CH$_2$)$_p$— wherein p is 1 to 4;

—(CH$_2$)$_a$—C(R$_D$R$_E$)(CH$_2$)$_b$—, wherein a and b are integers and a+b is 0 to 3, R$_D$ is hydrogen or alkyl of one to four carbon atoms, and R$_E$ is chosen from alkyl of one to four carbon atoms, hydroxy, —ORF wherein RF is alkyl of one to four carbon atoms, and —NR$_G$R'$_G$ wherein R$_G$ and R'$_G$ are independently hydrogen or alkyl of one to four carbon atoms; and —(CH$_2$)$_a$—(Y)—(CH$_2$)$_b$— wherein a and b are integers and a+b is 0 to 3, and Y is O, S, or —NR$_J$— wherein R$_J$ is hydrogen or alkyl of one to four carbon atoms;

and wherein q is 0 or 1 and R$_8$ is chosen from alkyl of one to four carbon atoms, alkoxy of one to four carbon atoms, and halogen, and pharmaceutically acceptable salts thereof.

In a further embodiment, the IRM compound can be chosen from thiazoloquinoline amines, oxazoloquinoline amines, thiazolonaphthyridine amines, thiazolopyridine amines, and oxazolopyridine amines of Formula IX:

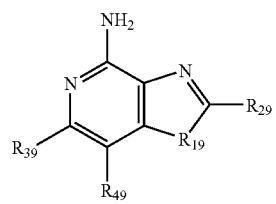

IX wherein:

R$_{19}$ is chosen from oxygen, sulfur and selenium;

R$_{29}$ is chosen from hydrogen;

alkyl;

alkyl-OH;

haloalkyl;

alkenyl;

alkyl-X-alkyl;

alkyl-X-alkenyl;

alkenyl-X-alkyl;

alkenyl-X-alkenyl;

alkyl-N(R$_{59}$)$_2$;

alkyl-N$_3$;

alkyl-O—C(O)—N(R$_{59}$)$_2$;

heterocyclyl;

alkyl-X-heterocyclyl;

alkenyl-X-heterocyclyl;

aryl;

alkyl-X-aryl;

alkenyl-X-aryl;

heteroaryl;

alkyl-X-heteroaryl; and alkenyl-X-heteroaryl;

R$_{39}$ and R$_{49}$ are each independently:

hydrogen;

X-alkyl;

halo;

haloalkyl;

N(R$_{59}$)$_2$;

or when taken together, R$_{39}$ and R$_{49}$ form a fused aromatic, heteroaromatic, cycloalkyl or heterocyclic ring;

X is chosen from —O—, —S—, —NR$_{59}$—, —C(O)—, —C(O)O—, —OC(O)—, and a bond; and each R$_{59}$ is independently H or C$_{1-8}$alkyl;

and pharmaceutically acceptable salts thereof.

In another embodiment, the IRM compound can be chosen from imidazonaphthyridine amines and imidazotetrahydronaphthyridine amines of Formulae X and XI below:

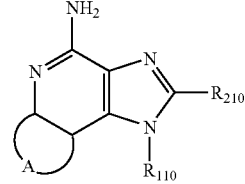

X wherein

A is =N—CR=CR—CR=; =CR—N=CR—CR=; =CR—CR=N—CR=; or =CR—CR=CR—N=;

R$_{110}$ is chosen from:

hydrogen;

—C$_{1-20}$ alkyl or C$_{2-20}$ alkenyl that is unsubstituted or substituted by one or more substituents chosen from:

aryl;

heteroaryl;

heterocyclyl;

O—C$_{1-20}$ alkyl,

O—(C$_{1-20}$ alkyl)$_{0-1}$aryl;

O—(C$_{1-20}$ alkyl)$_{0-1}$heteroaryl;

O—(C$_{1-20}$ alkyl)$_{0-1}$heterocyclyl;

CO—O—C$_{1-20}$ alkyl;

S(O)$_{0-2}$—C$_{1-20}$ alkyl;

S(O)$_{0-2}$—(C$_{1-20}$alkyl)$_{0-1}$aryl;
S(O)$_{0-2}$—(C$_{1-20}$alkyl)$_{0-1}$-heteroaryl;
S(O)$_{0-2}$—(C$_{1-20}$alkyl)$_{0-1}$-heterocyclyl;
N(R$_{310}$)$_2$;
N$_3$;
oxo;
halogen;
NO$_2$;
OH; and
SH; and
—C$_{1-20}$ alkyl-NR$_{310}$-Q-X—R$_{410}$ or —C$_{2-20}$ alkenyl-NR$_{310}$-Q-X—R$_{410}$ wherein Q is —CO— or —SO$_2$—; X is a bond, —O— or —NR$_{310}$— and R$_{410}$ is aryl; heteroaryl; heterocyclyl; or —C$_{1-20}$ alkyl or C$_{2-20}$ alkenyl that is unsubstituted or substituted by one or more substituents chosen from:
aryl;
heteroaryl;
heterocyclyl;
O—C$_{1-20}$ alkyl,
O—(C$_{1-20}$ alkyl)$_{0-1}$aryl;
O—(C$_{1-20}$ alkyl)$_{0-1}$heteroaryl;
O—(C$_{1-20}$ alkyl)$_{0-1}$heterocyclyl;
CO—O—C$_{1-20}$ alkyl;
S(O)$_{0-2}$—C$_{1-20}$ alkyl;
S(O)$_{0-2}$—(C$_{1-20}$alkyl)$_{0-1}$aryl;
S(O)$_{0-2}$—(C$_{1-20}$alkyl)$_{0-1}$-heteroaryl;
S(O)$_{0-2}$—(C$_{1-20}$alkyl)$_{0-1}$-heterocyclyl;
N(R$_{310}$)$_2$;
NR$_{310}$—CO—O—C$_{1-20}$ alkyl;
N$_3$;
oxo;
halogen;
NO$_2$;
OH; and
SH; or R$_{410}$ is

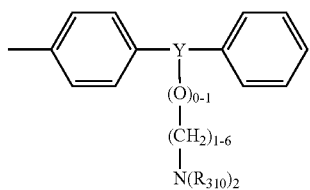

wherein Y is —N— or —CR—;
R$_{210}$ is chosen from:
hydrogen;
C$_{1-10}$ alkyl;
C$_{2-10}$ alkenyl;
aryl;
C$_{1-10}$ alkyl—O—C$_{1-10}$ alkyl;
C$_{1-10}$ alkyl-O—C$_{2-10}$ alkenyl; and
C$_{1-10}$ alkyl or C$_{2-10}$ alkenyl substituted by one or more substituents chosen from:
OH;
halogen;
N(R$_{310}$)$_2$;
CO—N(R$_{310}$)$_2$;
CO—C$_{1-10}$ alkyl;
N$_3$;
aryl;
heteroaryl;
heterocyclyl;
CO-aryl; and
CO-heteroaryl;

each R$_{310}$ is independently chosen from hydrogen and C$_{1-10}$ alkyl; and
each R is independently chosen from hydrogen, C$_{1-10}$ alkyl, C$_{1-10}$ alkoxy, halogen and trifluoromethyl, and pharmaceutically acceptable salts thereof,

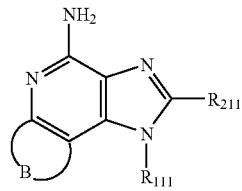

XI wherein
B is —NR—C(R)$_2$—C(R)$_2$—C(R)$_2$—; —C(R)$_2$—NR—C(R)$_2$—C(R)$_2$—; —C(R)$_2$—C(R)$_2$—NR—C(R)$_2$— or —C(R)$_2$—C(R)$_2$—C(R)$_2$—NR—;
R$_{111}$ is chosen from:
hydrogen;
C$_{1-20}$ alkyl or C$_{2-20}$ alkenyl that is unsubstituted or substituted by one or more substituents chosen from:
aryl;
heteroaryl;
heterocyclyl;
O—C$_{1-20}$ alkyl;
O—(C$_{1-20}$ alkyl)$_{0-1}$aryl;
O—(C$_{1-20}$ alkyl)$_{0-1}$heteroaryl;
O—(C$_{1-20}$ alkyl)$_{0-1}$heterocyclyl;
CO—O—C$_{1-20}$ alkyl;
S(O)$_{0-2}$—C$_{1-20}$ alkyl;
S(O)$_{0-2}$—(C$_{1-20}$alkyl)$_{0-1}$aryl;
S(O)$_{0-2}$—(C$_{1-20}$alkyl)$_{0-1}$heteroaryl;
S(O)$_{0-2}$—(C$_{1-20}$ alkyl)$_{0-1}$-heterocyclyl;
N(R$_{311}$)$_2$;
N$_3$;
oxo;
halogen;
NO$_2$;
OH; and
SH; and
—C$_{1-20}$ alkyl-NR$_{311}$-Q-X—R$_{411}$ or —C$_{2-20}$ alkenyl-NR$_{311}$-Q-X—R$_{411}$ wherein Q is —CO— or —SO$_2$—; X is a bond, —O— or —NR$_{311}$— and R$_{411}$ is aryl; heteroaryl; heterocyclyl; or —C$_{1-20}$ alkyl or C$_{2-20}$ alkenyl that is unsubstituted or substituted by one or more substituents chosen from:
aryl;
heteroaryl;
heterocyclyl;
O—C$_{1-20}$ alkyl,
O—(C$_{1-20}$ alkyl)$_{0-1}$aryl;
O—(C$_{1-20}$ alkyl)$_{0-1}$heteroaryl;
O—(C$_{1-20}$ alkyl)$_{0-1}$-heterocyclyl;
CO—O—C$_{1-20}$ alkyl;
S(O)$_{0-2}$—C$_{1-20}$ alkyl;
S(O)$_{0-2}$—(C$_{1-20}$ alkyl)$_{0-1}$aryl;
S(O)$_{0-2}$—(C$_{1-20}$alkyl)$_{0-1}$heteroaryl;
S(O)$_{0-2}$—(C$_{1-20}$alkyl)$_{0-1}$heterocyclyl;
N(R$_{311}$)$_2$;
NR$_{311}$—CO—O—C$_{1-20}$ alkyl;
N$_3$;
oxo;
halogen;

NO₂;
OH; and
SH; or R₄₁₁ is

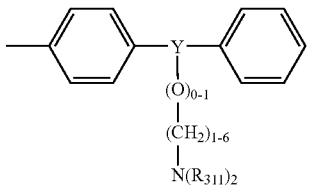

wherein Y is —N— or —CR—;
R₂₁₁ is chosen from:
hydrogen;
$C_{1-10}$ alkyl;
$C_{2-10}$ alkenyl;
aryl
$C_{1-10}$ alkyl —O—$C_{1-10}$-alkyl;
$C_{1-10}$ alkyl-O—$C_{2-10}$ alkenyl; and
$C_{1-10}$ alkyl or $C_{2-10}$ alkenyl substituted by one or more substituents chosen from:
OH;
halogen;
N(R₃₁₁)₂;
CO—N(R₃₁₁)₂;
CO—$C_{1-10}$ alkyl;
N₃;
aryl;
heteroaryl;
heterocyclyl;
CO-aryl; and
CO-heteroaryl;
each R₃₁₁ is independently chosen from hydrogen and $C_{1-10}$ alkyl; and
each R is independently chosen from hydrogen, $C_{1-10}$ alkyl, $C_{1-10}$ alkoxy, halogen and trifluoromethyl,
and pharmaceutically acceptable salts thereof.

In a further embodiment, the IRM compound can be chosen from imidazoquinoline amines and imidazotetrahydroquinoline amines, for example, 1H-imidazo[4,5-c]quinolin-4-amines and tetrahydro-1H-imidazo[4,5-c]quinolin-4-amines defined by Formulas XII, XIII and XIV below:

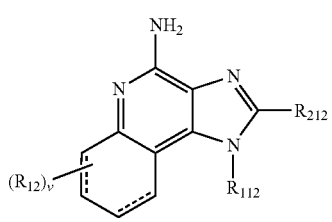

XII wherein
R₁₁₂ is -alkyl-NR₃₁₂—CO—R₄₁₂ or -alkenyl-NR₃₁₂—CO—R₄₁₂ wherein R₄₁₂ is aryl, heteroaryl, alkyl or alkenyl, each of which may be unsubstituted or substituted by one or more substituents chosen from:
alkyl;
alkenyl;
alkynyl;
(alkyl)₀₋₁aryl;
(alkyl)₀₋₁-(substituted aryl);
(alkyl)₀₋₁heteroaryl;
(alkyl)₀₋₁-(substituted heteroaryl);
O-alkyl;
O-(alkyl)₀₋₁aryl;
O-(alkyl)₀₋₁-(substituted aryl);
O-(alkyl)₀₋₁heteroaryl;
O-(alkyl)₀₋₁-(substituted heteroaryl);
CO-aryl;
CO-(substituted aryl);
CO-heteroaryl;
CO-(substituted heteroaryl);
COOH;
CO—O-alkyl;
CO-alkyl;
S(O)₀₋₂-alkyl;
S(O)₀₋₂-(alkyl)₀₋₁aryl;
S(O)₀₋₂-(alkyl)₀₋₁-(substituted aryl);
S(O)₀₋₂-(alkyl)₀₋₁heteroaryl;
S(O)₀₋₂-(alkyl)₀₋₁-(substituted heteroaryl);
P(O)(OR₃₁₂)₂;
NR₃₁₂—CO—O-alkyl;
N₃;
halogen;
NO₂;
CN;
haloalkyl;
O-haloalkyl;
CO-haloalkyl;
OH;
SH; and in the case of alkyl, alkenyl, or heterocyclyl, oxo;
or R₄₁₂ is

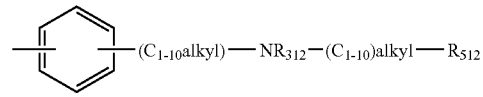

wherein R₅₁₂ is an aryl, (substituted aryl), heteroaryl, (substituted heteroaryl), heterocyclyl or (substituted heterocyclyl) group;
R₂₁₂ is chosen from:
hydrogen;
alkyl;
alkenyl;
aryl;
(substituted aryl);
heteroaryl;
(substituted heteroaryl);
heterocyclyl;
(substituted heterocyclyl);
alkyl —O-alkyl;
alkyl-O-alkenyl; and
alkyl or alkenyl substituted by one or more substituents chosen from:
OH;
halogen;
N(R₃₁₂)₂;
CO—N(R₃₁₂)₂;
CO—$C_{1-10}$ alkyl;
CO—O—$C_{1-10}$ alkyl;
N₃;
aryl;
(substituted aryl);
heteroaryl;
(substituted heteroaryl);
heterocyclyl;

(substituted heterocyclyl);
CO-aryl; and
CO-heteroaryl;
each $R_{312}$ is independently chosen from hydrogen; $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{1-10}$ alkyl;
v is 0 to 4;
and each $R_{12}$ present is independently chosen from $C_{1-10}$ alkyl, $C_{1-10}$ alkoxy, halogen and trifluoromethyl;

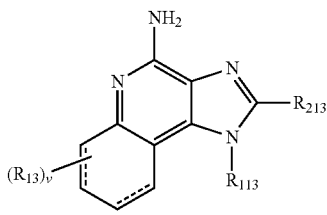

XIII wherein
$R_{113}$ is -alkyl-$NR_{313}$—$SO_2$—X—$R_{413}$ or -alkenyl-$NR_{313}$—$SO_2$—X—$R_{413}$;
X is a bond or —$NR_{513}$—;
$R_{413}$ is aryl, heteroaryl, heterocyclyl, alkyl or alkenyl, each of which may be unsubstituted or substituted by one or more substituents chosen from:
alkyl;
alkenyl;
aryl;
heteroaryl;
heterocyclyl;
substituted cycloalkyl;
substituted aryl;
substituted heteroaryl;
substituted heterocyclyl;
O-alkyl;
O-(alkyl)$_{0-1}$aryl;
O-(alkyl)$_{0-1}$-substituted aryl;
O-(alkyl)$_{0-1}$heteroaryl;
O-(alkyl)$_{0-1}$-substituted heteroaryl;
O-(alkyl)$_{0-1}$-heterocyclyl;
O-(alkyl)$_{0-1}$-substituted heterocyclyl;
COOH;
CO—O-alkyl;
CO-alkyl;
$S(O)_{0-2}$-alkyl;
$S(O)_{0-2}$-(alkyl)$_{0-1}$aryl;
$S(O)_{0-2}$-(alkyl)$_{0-1}$-substituted aryl;
$S(O)_{0-2}$-(alkyl)$_{0-1}$heteroaryl;
$S(O)_{0-2}$-(alkyl)$_{0-1}$-substituted heteroaryl;
$S(O)_{0-2}$-(alkyl)$_{0-1}$heterocyclyl;
$S(O)_{0-2}$-(alkyl)$_{0-1}$-substituted heterocyclyl;
(alkyl)$_{0-1}$-$NR_{313}R_{313}$;
(alkyl)$_{0-1}$-$NR_{313}$—CO—O-alkyl;
(alkyl)$_{0-1}$-$NR_{313}$—CO-alkyl;
(alkyl)$_{0-1}$-$NR_{313}$—CO-aryl;
(alkyl)$_{0-1}$-$NR_{313}$—CO-substituted aryl;
(alkyl)$_{0-1}$-$NR_{313}$—CO-heteroaryl;
(alkyl)$_{0-1}$-$NR_{313}$—CO-substituted heteroaryl;
$N_3$;
halogen;
haloalkyl;
haloalkoxy;
CO-haloalkyl;
CO-haloalkoxy;
$NO_2$;
CN;
OH;
SH; and in the case that $R_{413}$ is alkyl, alkenyl, or heterocyclyl, oxo;
$R_{213}$ is chosen from:
hydrogen;
alkyl;
alkenyl;
aryl;
substituted aryl;
heteroaryl;
substituted heteroaryl;
alkyl-O-alkyl;
alkyl-O— alkenyl; and
alkyl or alkenyl substituted by one or more substituents chosen from:
OH;
halogen;
$N(R_{313})_2$;
CO—$N(R_{313})_2$;
CO—$C_{1-10}$ alkyl;
CO—O—$C_{1-10}$ alkyl;
$N_3$;
aryl;
substituted aryl;
heteroaryl;
substituted heteroaryl;
heterocyclyl;
substituted heterocyclyl;
CO-aryl;
CO-(substituted aryl);
CO-heteroaryl; and
CO-(substituted heteroaryl);
each $R_{313}$ is independently chosen from hydrogen, $C_{1-10}$ alkyl, and when X is a bond $R_{313}$ and $R_{413}$ can combine to form a 3 to 7 membered heterocyclic or substituted heterocyclic ring;
$R_{513}$ is chosen from hydrogen, $C_{1-10}$ alkyl, and $R_{413}$ and $R_{513}$ can combine to form a 3 to 7 membered heterocyclic or substituted heterocyclic ring;
v is 0 to 4 and each $R_{13}$ present is independently chosen from $C_{1-10}$ alkyl, $C_{1-10}$ alkoxy, halogen and trifluoromethyl;

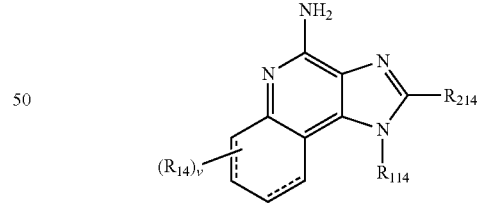

XIV wherein
$R_{114}$ is -alkyl-$NR_{314}$—CY—$NR_{514}$—X—$R_{414}$ or -alkenyl-$NR_{314}$—CY—$NR_{514}$—X—$R_{414}$ wherein
Y is =O or =S;
X is a bond, —CO— or —$SO_2$—;
$R_{414}$ is aryl, heteroaryl, heterocyclyl, alkyl or alkenyl, each of which may be unsubstituted or substituted by one or more substituents chosen from:
alkyl;
alkenyl;
aryl;
heteroaryl;

heterocyclyl;
substituted aryl;
substituted heteroaryl;
substituted heterocyclyl;
O-alkyl;
O-(alkyl)$_{0-1}$aryl;
O-(alkyl)$_{0-1}$-substituted aryl;
O-(alkyl)$_{0-1}$heteroaryl;
O-(alkyl)$_{0-1}$-substituted heteroaryl;
O-(alkyl)$_{0-1}$-heterocyclyl;
O-(alkyl)$_{0-1}$-substituted heterocyclyl;
COOH;
CO—O-alkyl;
CO-alkyl;
S(O)$_{0-2}$-alkyl;
S(O)$_{0-2}$-(alkyl)$_{0-1}$aryl;
S(O)$_{0-2}$-(alkyl)$_{0-1}$-substituted aryl;
S(O)$_{0-2}$-(alkyl)$_{0-1}$heteroaryl;
S(O)$_{0-2}$-(alkyl)$_{0-1}$-substituted heteroaryl;
S(O)$_{0-2}$-(alkyl)$_{0-1}$heterocyclyl;
S(O)$_{0-2}$-(alkyl)$_{0-1}$-substituted heterocyclyl;
(alkyl)$_{0-1}$-NR$_{314}$R$_{314}$;
(alkyl)$_{0-1}$-NR$_{314}$—CO—O-alkyl;
(alkyl)$_{0-1}$-NR$_{314}$—CO-alkyl;
(alkyl)$_{0-1}$-NR$_{314}$—CO-aryl;
(alkyl)$_{0-1}$-NR$_{314}$—CO-substituted aryl;
(alkyl)$_{0-1}$-NR$_{314}$—CO-heteroaryl;
(alkyl)$_{0-1}$-NR$_{314}$—CO-substituted heteroaryl;
N$_3$;
halogen;
haloalkyl;
haloalkoxy;
CO-haloalkoxy;
NO$_2$;
CN;
OH;
SH; and, in the case that R$_{414}$ is alkyl, alkenyl or heterocyclyl, oxo; with the proviso that when X is a bond R$_{414}$ can additionally be hydrogen;
R$_{214}$ is chosen from:
hydrogen;
alkyl;
alkenyl;
aryl;
substituted aryl;
heteroaryl;
substituted heteroaryl;
alkyl—O-alkyl;
alkyl-O— alkenyl; and
alkyl or alkenyl substituted by one or more substituents chosen from:
—OH;
halogen;
N(R$_{314}$)$_2$;
CO—N(R$_{314}$)$_2$;
CO—C$_{1-10}$ alkyl;
CO—O—C$_{1-10}$ alkyl;
N$_3$;
aryl;
substituted aryl;
heteroaryl;
substituted heteroaryl;
heterocyclyl;
substituted heterocyclyl;
CO-aryl;
CO-(substituted aryl);
CO-heteroaryl; and
CO-(substituted heteroaryl);
each R$_{314}$ is independently chosen from hydrogen and C$_{1-10}$ alkyl;
R$_{514}$ is chosen from hydrogen, C$_{1-10}$ alkyl, and R$_{414}$ and R$_{514}$ can combine to form a 3 to 7 membered heterocyclic or substituted heterocyclic ring;
v is 0 to 4 and each R$_{14}$ present is independently chosen from C$_{1-10}$ alkyl, C$_{1-10}$ alkoxy, halogen and trifluoromethyl, and pharmaceutically acceptable salts thereof.

In yet another embodiment, the IRM compound can be chosen from imidazoquinoline amines and imidazotetrahydroquinoline amines, for example, 1H-imidazo[4,5-c]quinolin-4-amines and tetrahydro-1H-imidazo[4,5-c]quinolin-4-amines defined by Formulas XV, XVI, XVII, XVIII, XIX, XX, XXI, XXII, XXIII, XXIV, XXV, and XXVI below

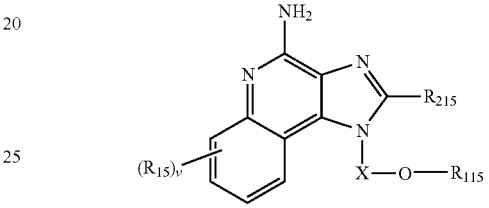

XV wherein:
X is —CHR$_{515}$—, —CHR$_{515}$-alkyl-, or —CHR$_{515}$-alkenyl-;
R$_{115}$ is chosen from:
R$_{415}$—CR$_{315}$-Z-R$_{615}$-alkyl;
R$_{415}$—CR$_{315}$-Z-R$_{615}$-alkenyl;
R$_{415}$—CR$_{315}$-Z-R$_{615}$-aryl;
R$_{415}$—CR$_{315}$-Z-R$_{615}$-heteroaryl;
R$_{415}$—CR$_{315}$-Z-R$_{615}$-heterocyclyl;
R$_{415}$—CR$_{315}$-Z—H;
R$_{415}$—NR$_{715}$—CR$_{315}$-R$_{615}$-alkyl;
R$_{415}$—NR$_{715}$—CR$_{315}$-R$_{615}$-alkenyl;
R$_{415}$—NR$_{715}$—CR$_{315}$-R$_{615}$-aryl;
R$_{415}$—NR$_{715}$—CR$_{315}$-R$_{615}$-heteroaryl;
R$_{415}$—NR$_{715}$—CR$_{315}$-R$_{615}$-heterocyclyl; and
R$_{415}$—NR$_{715}$—CR$_{315}$-R$_{815}$;
Z is —NR$_{515}$—, —O—, or —S—;
R$_{215}$ is chosen from:
hydrogen;
alkyl;
alkenyl;
aryl;
heteroaryl;
heterocyclyl;
alkyl-Y-alkyl;
alkyl-Y-alkenyl;
alkyl-Y-aryl; and
alkyl or alkenyl substituted by one or more substituents selected from the group consisting of:
OH;
halogen;
N(R$_{515}$)$_2$;
CO—N(R$_{515}$)$_2$;
CO—C$_{1-10}$ alkyl;
CO—O—C$_{1-10}$ alkyl;
N$_3$;
aryl;
heteroaryl;
heterocyclyl;
CO-aryl; and
CO-heteroaryl;

$R_{315}$ is =O or =S;
$R_{415}$ is alkyl or alkenyl, which may be interrupted by one or more —O— groups;
each $R_{515}$ is independently H or $C_{1-10}$ alkyl;
$R_{615}$ is a bond, alkyl, or alkenyl, which may be interrupted by one or more —O— groups;
$R_{715}$ is H, $C_{1-10}$ alkyl, arylalkyl, or $R_{415}$ and $R_{715}$ can join together to form a 5 to 7 membered heterocylcic ring;
$R_{815}$ is H, $C_{1-10}$ alkyl, or $R_{715}$ and $R_{815}$ can join together to form a 5 to 7 membered heterocyclic ring;
Y is —O— or —S(O)$_{0-2}$—;
v is 0 to 4; and
each $R_{15}$ present is independently chosen from $C_{1-10}$ alkyl, $C_{1-10}$ alkoxy, hydroxy, halogen and trifluoromethyl;

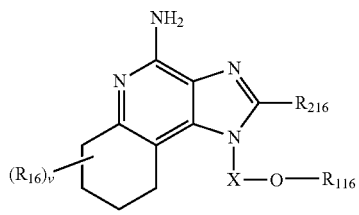

XVI wherein:
X is —CHR$_{516}$—, —CHR$_{516}$-alkyl-, or —CHR$_{516}$-alkenyl-;
$R_{116}$ is chosen from:
 $R_{416}$—CR$_{316}$-Z-R$_{616}$-alkyl;
 $R_{416}$—CR$_{316}$-Z-R$_{616}$-alkenyl;
 $R_{416}$—CR$_{316}$-Z-R$_{616}$-aryl;
 $R_{416}$—CR$_{316}$-Z-R$_{616}$-heteroaryl;
 $R_{416}$—CR$_{316}$-Z-R$_{616}$-heterocyclyl;
 $R_{416}$—CR$_{316}$-Z—H;
 $R_{416}$—NR$_{716}$—CR$_{316}$-R$_{616}$-alkyl;
 $R_{416}$—NR$_{716}$—CR$_{316}$-R$_{616}$-alkenyl;
 $R_{416}$—NR$_{716}$—CR$_{316}$-R$_{616}$-aryl;
 $R_{416}$—NR$_{716}$—CR$_{316}$-R$_{616}$-heteroaryl;
 $R_{416}$—NR$_{716}$—CR$_{316}$-R$_{616}$-heterocyclyl; and
 $R_{416}$—NR$_{716}$—CR$_{316}$-R$_{816}$;
Z is —NR$_{516}$—, —O—, or —S—;
$R_{216}$ is chosen from:
 hydrogen;
 alkyl;
 alkenyl;
 aryl;
 heteroaryl;
 heterocyclyl;
 alkyl-Y-alkyl;
 alkyl-Y-alkenyl;
 alkyl-Y-aryl; and
 alkyl or alkenyl substituted by one or more substituents chosen from:
  OH;
  halogen;
  N(R$_{516}$)$_2$;
  CO—N(R$_{516}$)$_2$;
  CO—C$_{1-10}$ alkyl;
  CO—O—C$_{1-10}$ alkyl;
  N$_3$;
  aryl;
  heteroaryl;
  heterocyclyl;
  CO-aryl; and
  CO-heteroaryl;

$R_{316}$ is =O or =S;
$R_{416}$ is alkyl or alkenyl, which may be interrupted by one or more —O— groups;
each $R_{516}$ is independently H or $C_{1-10}$ alkyl;
$R_{616}$ is a bond, alkyl, or alkenyl, which may be interrupted by one or more —O— groups;
$R_{716}$ is H, $C_{1-10}$ alkyl, arylalkyl, or $R_{416}$ and $R_{716}$ can join together to form a 5 to 7 membered heterocyclic ring;
$R_{816}$ is H or $C_{1-10}$ alkyl; or $R_{716}$ and $R_{816}$ can join together to form a 5 to 7 membered heterocyclic ring;
Y is —O— or —S(O)$_{0-2}$—;
v is 0 to 4; and
each $R_{16}$ present is independently chosen from $C_{1-10}$ alkyl, $C_{1-10}$ alkoxy, hydroxy, halogen, and trifluoromethyl;

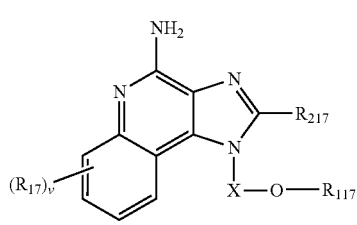

XVII wherein:
X is —CHR$_{317}$—, —CHR$_{317}$-alkyl-, or —CHR$_{317}$-alkenyl-;
$R_{117}$ is chosen from:
 alkenyl;
 aryl; and
 $R_{417}$-aryl;
$R_{217}$ is chosen from:
 hydrogen;
 alkyl;
 alkenyl;
 aryl;
 heteroaryl;
 heterocyclyl;
 alkyl-Y-alkyl;
 alkyl-Y-alkenyl;
 alkyl-Y-aryl; and
 alkyl or alkenyl substituted by one or more substituents chosen from:
  OH;
  halogen;
  N(R$_{317}$)$_2$;
  CO—N(R$_{317}$)$_2$;
  CO—C$_{1-10}$ alkyl;
  CO—O—C$_{1-10}$ alkyl;
  N$_3$;
  aryl;
  heteroaryl;
  heterocyclyl;
  CO-aryl; and
  CO-heteroaryl;
$R_{417}$ is alkyl or alkenyl, which may be interrupted by one or more —O— groups;
each $R_{317}$ is independently H or $C_{1-10}$ alkyl;
each Y is independently —O— or —S(O)$_{0-2}$—;
v is 0 to 4; and
each $R_{17}$ present is independently chosen from $C_{1-10}$ alkyl, $C_{1-10}$ alkoxy, hydroxy, halogen and trifluoromethyl;

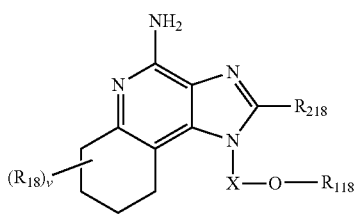

XVIII wherein:
X is —CHR$_{318}$—, —CHR$_{318}$-alkyl-, or —CHR$_{318}$-alkenyl-;
R$_{118}$ is chosen from:
  aryl;
  alkenyl; and
  —R$_{418}$-aryl;
R$_{218}$ is chosen from:
  hydrogen;
  alkyl;
  alkenyl;
  aryl;
  heteroaryl;
  heterocyclyl;
  alkyl-Y-alkyl;
  alkyl-Y-aryl;
  alkyl-Y-alkenyl; and
  alkyl or alkenyl substituted by one or more substituents chosen from:
    OH;
    halogen;
    N(R$_{318}$)$_2$;
    CO—N(R$_{318}$)$_2$;
    CO—C$_{1-10}$ alkyl;
    CO—O—C$_{1-10}$ alkyl;
    N$_3$;
    aryl;
    heteroaryl;
    heterocyclyl;
    CO-aryl; and
    CO-heteroaryl;
R$_{418}$ is alkyl or alkenyl, which may be interrupted by one or more —O— groups;
each R$_{318}$ is independently H or C$_{1-10}$ alkyl;
each Y is independently —O— or —S(O)$_{0-2}$—;
v is 0 to 4; and
each R$_{18}$ present is independently chosen from C$_{1-10}$ alkyl, C$_{1-10}$ alkoxy, hydroxy, halogen and trifluoromethyl;

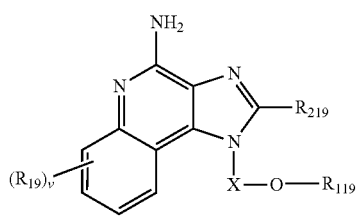

XIX wherein:
X is —CHR$_{319}$—, —CHR$_{319}$-alkyl-, or —CHR$_{319}$-alkenyl-;
R$_{119}$ is chosen from:
  heteroaryl;
  heterocyclyl;
  R$_{419}$-heteroaryl; and
  R$_{419}$-heterocyclyl;
R$_{219}$ is chosen from:
  hydrogen;
  alkyl;
  alkenyl;
  aryl;
  heteroaryl;
  heterocyclyl;
  alkyl-Y-alkyl;
  alkyl-Y-alkenyl;
  alkyl-Y-aryl; and
  alkyl or alkenyl substituted by one or more substituents chosen from:
    OH;
    halogen;
    N(R$_{319}$)$_2$;
    CO—N(R$_{319}$)$_2$;
    CO—C$_{1-10}$ alkyl;
    CO—O—C$_{1-10}$ alkyl;
    N$_3$;
    aryl;
    heteroaryl;
    heterocyclyl;
    CO-aryl; and
    CO-heteroaryl;
R$_{419}$ is alkyl or alkenyl, which may be interrupted by one or more —O— groups;
each R$_{319}$ is independently H or C$_{1-10}$ alkyl;
each Y is independently —O— or —S(O)$_{0-2}$—;
v is 0 to 4; and
each R$_{19}$ present is independently chosen from C$_{1-10}$ alkyl, C$_{1-10}$ alkoxy, hydroxy, halogen and trifluoromethyl;

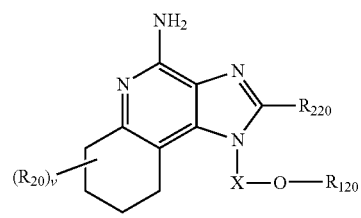

XX wherein:
X is —CHR$_{320}$—, —CHR$_{320}$-alkyl-, or —CHR$_{320}$-alkenyl-;
R$_{120}$ is chosen from:
  heteroaryl;
  heterocyclyl;
  R$_{420}$-heteroaryl; and
  R$_{420}$-heterocyclyl;
R$_{220}$ is chosen from:
  hydrogen;
  alkyl;
  alkenyl;
  aryl;
  heteroaryl;
  heterocyclyl;
  alkyl-Y-alkyl;
  alkyl-Y-alkenyl;

alkyl-Y-aryl; and
alkyl or alkenyl substituted by one or more substituents
  chosen from:
    OH;
    halogen;
    $N(R_{320})_2$;
    $CO-N(R_{320})_2$;
    $CO-C_{1-10}$ alkyl;
    $CO-O-C_{1-10}$ alkyl;
    $N_3$;
    aryl;
    heteroaryl;
    heterocyclyl;
    CO-aryl; and
    CO-heteroaryl;
$R_{420}$ is alkyl or alkenyl, which may be interrupted by one or more —O— groups;
each $R_{320}$ is independently H or $C_{1-10}$ alkyl;
each Y is independently —O— or —$S(O)_{0-2}$—;
v is 0 to 4; and
each $R_{20}$ present is independently chosen from $C_{1-10}$ alkyl, $C_{1-10}$ alkoxy, hydroxy, halogen and trifluoromethyl;

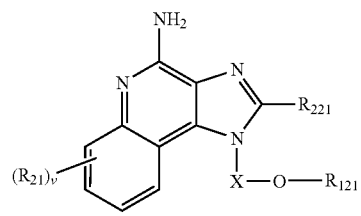

XXI wherein:
X is —$CHR_{521}$—, —$CHR_{521}$-alkyl-, or —$CHR_{521}$-alkenyl-;
$R_{121}$ is chosen from:
  $R_{421}-NR_{321}-SO_2-R_{621}$-alkyl;
  $R_{421}-NR_{321}-SO_2-R_{621}$-alkenyl;
  $R_{421}-NR_{321}-SO_2-R_{621}$-aryl;
  $R_{421}-NR_{321}-SO_2-R_{621}$-heteroaryl;
  $R_{421}-NR_{321}-SO_2-R_{621}$-heterocyclyl;
  $R_{421}-NR_{321}-SO_2-R_{721}$;
  $R_{421}-NR_{321}-SO_2-NR_{521}-R_{621}$-alkyl;
  $R_{421}-NR_{321}-SO_2-NR_{521}-R_{621}$-alkenyl;
  $R_{421}-NR_{321}-SO_2-NR_{521}-R_{621}$-aryl;
  $R_{421}-NR_{321}-SO_2-NR_{521}-R_{621}$-heteroaryl;
  $R_{421}-NR_{321}-SO_2-NR_{521}-R_{621}$-heterocyclyl; and
  $R_{421}-NR_{321}-SO_2-NH_2$;
$R_{221}$ is chosen from:
  hydrogen;
  alkyl;
  alkenyl;
  aryl;
  heteroaryl;
  heterocyclyl;
  alkyl-Y-alkyl;
  alkyl-Y-alkenyl;
  alkyl-Y-aryl; and
  alkyl or alkenyl substituted by one or more substituents
    chosen from:
      OH;
      halogen;
      $N(R_{521})_2$;
      $CO-N(R_{521})_2$;
      $CO-C_{1-10}$ alkyl;
      $CO-O-C_{1-10}$ alkyl;
      $N_3$;
      aryl;
      heteroaryl;
      heterocyclyl;
      CO-aryl; and
      CO-heteroaryl;
Y is —O— or —$S(O)_{0-2}$—;
$R_{321}$ is H, $C_{1-10}$ alkyl, or arylalkyl;
each $R_{421}$ is independently alkyl or alkenyl, which may be interrupted by one or more —O— groups, or $R_{321}$ and $R_{421}$ can join together to form a 5 to 7 membered heterocyclic ring;
each $R_{521}$ is independently H, $C_{1-10}$ alkyl, or $C_{2-10}$ alkenyl;
$R_{621}$ is a bond, alkyl, or alkenyl, which may be interrupted by one or more —O— groups;
$R_{721}$ is $C_{1-10}$ alkyl, or $R_{321}$ and $R_{721}$ can join together to form a 5 to 7 membered heterocyclic ring;
v is 0 to 4; and
each $R_{21}$ present is independently chosen from $C_{1-10}$ alkyl, $C_{1-10}$ alkoxy, hydroxy, halogen and trifluoromethyl;

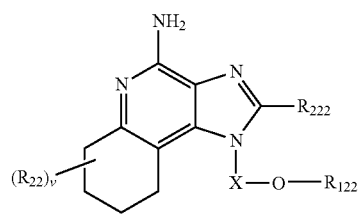

XXII wherein:
X is —$CHR_{522}$—, —$CHR_{522}$-alkyl-, or —$CHR_{522}$-alkenyl-;
$R_{122}$ is chosen from:
  $R_{422}-NR_{322}-SO_2-R_{622}$-alkyl;
  $R_{422}-NR_{322}-SO_2-R_{622}$-alkenyl;
  $R_{422}-NR_{322}-SO_2-R_{622}$-aryl;
  $R_{422}-NR_{322}-SO_2-R_{622}$-heteroaryl;
  $R_{422}-NR_{322}-SO_2-R_{622}$-heterocyclyl;
  $R_{422}-NR_{322}-SO_2-R_{722}$;
  $R_{422}-NR_{322}-SO_2-NR_{522}-R_{622}$-alkyl;
  $R_{422}-NR_{322}-SO_2-NR_{522}-R_{622}$-alkenyl;
  $R_{422}-NR_{322}-SO_2-NR_{522}-R_{622}$-aryl;
  $R_{422}-NR_{322}-SO_2-NR_{522}-R_{622}$-heteroaryl;
  $R_{422}-NR_{322}-SO_2-NR_{522}-R_{622}$-heterocyclyl; and
  $R_{422}-NR_{322}-SO_2-NH_2$;
$R_{222}$ is chosen from:
  hydrogen;
  alkyl;
  alkenyl;
  aryl;
  heteroaryl;
  heterocyclyl;
  alkyl-Y-alkyl;
  alkyl-Y-alkenyl;
  alkyl-Y-aryl; and
  alkyl or alkenyl substituted by one or more substituents
    chosen from:
      OH;
      halogen;
      $N(R_{522})_2$;
      $CO-N(R_{522})_2$;
      $CO-C_{1-10}$ alkyl;
      $CO-O-C_{1-10}$ alkyl;

N₃;
aryl;
heteroaryl;
heterocyclyl;
CO-aryl; and
CO-heteroaryl;
Y is —O— or —S(O)$_{0-2}$—;
R$_{322}$ is H, C$_{1-10}$ alkyl, or arylalkyl;
each R$_{422}$ is independently alkyl or alkenyl, which may be interrupted by one or more —O— groups, or R$_{322}$ and R$_{422}$ can join together to form a 5 to 7 membered heterocyclic ring;
each R$_{522}$ is independently H, C$_{1-10}$ alkyl, or C$_{2-10}$ alkenyl;
R$_{622}$ is a bond, alkyl, or alkenyl, which may be interrupted by one or more —O— groups;
R$_{722}$ is C$_{1-10}$ alkyl, or R$_{322}$ and R$_{722}$ can join together to form a 5 to 7 membered heterocyclic ring;
v is 0 to 4; and
each R$_{22}$ present is independently chosen from C$_{1-10}$ alkyl, C$_{1-10}$ alkoxy, hydroxy, halogen, and trifluoromethyl;

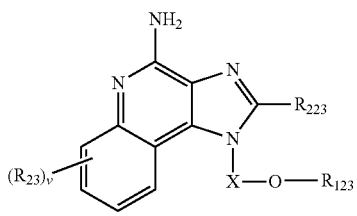

XXIII wherein:
X is —CHR$_{323}$—, —CHR$_{323}$-alkyl-, or —CHR$_{323}$-alkenyl-;
Z is —S—, —SO—, or —SO$_2$—;
R$_{123}$ is chosen from:
  alkyl;
  aryl;
  heteroaryl;
  heterocyclyl;
  alkenyl;
  R$_{423}$-aryl;
  R$_{423}$-heteroaryl;
  R$_{423}$-heterocyclyl;
R$_{223}$ is chosen from:
  hydrogen;
  alkyl;
  alkenyl;
  aryl;
  heteroaryl;
  heterocyclyl;
  alkyl-Y-alkyl;
  alkyl-Y-alkenyl;
  alkyl-Y-aryl; and
  alkyl or alkenyl substituted by one or more substituents chosen from:
    OH;
    halogen;
    N(R$_{323}$)$_2$;
    CO—N(R$_{323}$)$_2$;
    CO—C$_{1-10}$ alkyl;
    CO—O—C$_{1-10}$ alkyl;
    N$_3$;
    aryl;
    heteroaryl;
    heterocyclyl;
    CO-aryl; and
    CO-heteroaryl;
each R$_{323}$ is independently H or C$_{1-10}$ alkyl;
each R$_{423}$ is independently alkyl or alkenyl;
each Y is independently —O— or —S(O)$_{0-2}$—;
v is 0 to 4; and
each R$_{23}$ present is independently chosen from C$_{1-10}$ alkyl, C$_{1-10}$ alkoxy, hydroxy, halogen and trifluoromethyl;

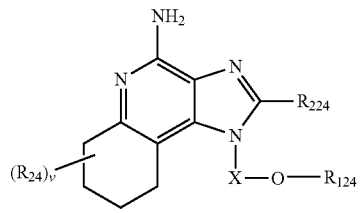

XXIV wherein:
X is —CHR$_{324}$—, —CHR$_{324}$-alkyl-, or —CHR$_{324}$-alkenyl-;
Z is —S—, —SO—, or —SO$_2$—;
R$_{124}$ is chosen from:
  alkyl;
  aryl;
  heteroaryl;
  heterocyclyl;
  alkenyl;
  R$_{424}$-aryl;
  R$_{424}$-heteroaryl; and
  R$_{424}$-heterocyclyl;
R$_{224}$ is chosen from:
  hydrogen;
  alkyl;
  alkenyl;
  aryl;
  heteroaryl;
  heterocyclyl;
  alkyl-Y-alkyl;
  alkyl-Y-alkenyl;
  alkyl-Y-aryl; and
  alkyl or alkenyl substituted by one or more substituent chosen from:
    OH;
    halogen;
    N(R$_{324}$)$_2$;
    CO—N(R$_{324}$)$_2$;
    CO—C$_{1-10}$ alkyl;
    CO—O—C$_{1-10}$ alkyl;
    N$_3$;
    aryl;
    heteroaryl;
    heterocyclyl;
    CO-aryl; and
    CO-heteroaryl;
each R$_{324}$ is independently H or C$_{1-10}$ alkyl;
each R$_{424}$ is independently alkyl or alkenyl;
each Y is independently —O— or —S(O)$_{0-2}$—;
v is 0 to 4; and
each R$_{24}$ present is independently chosen from C$_{1-10}$ alkyl, C$_{1-10}$ alkoxy, hydroxy, halogen and trifluoromethyl;

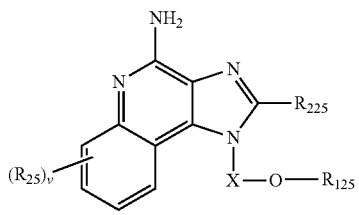

XXV wherein:
X is —CHR$_{525}$—, —CHR$_{525}$-alkyl-, or —CHR$_{525}$-alkenyl-;
R$_{125}$ is chosen from:
  R$_{425}$—NR$_{825}$—CR$_{325}$—NR$_{525}$-Z-R$_{625}$-alkyl;
  R$_{425}$—NR$_{825}$—CR$_{325}$—NR$_{525}$-Z-R$_{625}$-alkenyl;
  R$_{425}$—NR$_{825}$—CR$_{325}$—NR$_{525}$-Z-R$_{625}$-aryl;
  R$_{425}$—NR$_{825}$—CR$_{325}$—NR$_{525}$-Z-R$_{625}$-heteroaryl;
  R$_{425}$—NR$_{825}$—CR$_{325}$—NR$_{525}$-Z-R$_{625}$-heterocyclyl;
  R$_{425}$—NR$_{825}$—CR$_{325}$—NR$_{525}$R$_{725}$;
  R$_{425}$—NR$_{825}$—CR$_{325}$—NR$_{925}$-Z-R$_{625}$-alkyl;
  R$_{425}$—NR$_{825}$—CR$_{325}$—NR$_{925}$-Z-R$_{625}$-alkenyl;
  R$_{425}$—NR$_{825}$—CR$_{325}$—NR$_{925}$-Z-R$_{625}$-aryl;
  R$_{425}$—NR$_{825}$—CR$_{325}$—NR$_{925}$-Z-R$_{625}$-heteroaryl; and
  R$_{425}$—NR$_{825}$—CR$_{325}$—NR$_{925}$-Z-R$_{625}$-heterocyclyl;
R$_{225}$ is chosen from:
  hydrogen;
  alkyl;
  alkenyl;
  aryl;
  heteroaryl;
  heterocyclyl;
  alkyl-Y-alkyl;
  alkyl-Y-alkenyl;
  alkyl-Y-aryl; and
  alkyl or alkenyl substituted by one or more substituents chosen from:
    OH;
    halogen;
    N(R$_{525}$)$_2$;
    CO—N(R$_{525}$)$_2$;
    CO—C$_{1-10}$ alkyl;
    CO—O—C$_{1-10}$ alkyl;
    N$_3$;
    aryl;
    heteroaryl;
    heterocyclyl;
    CO-aryl; and
    CO-heteroaryl;
each R$_{325}$ is =O or =S;
each R$_{425}$ is independently alkyl or alkenyl, which may be interrupted by one or more —O— groups;
each R$_{525}$ is independently H or C$_{1-10}$ alkyl;
R$_{625}$ is a bond, alkyl, or alkenyl, which may be interrupted by one or more —O— groups;
R$_{725}$ is H, C$_{1-10}$ alkyl which may be interrupted by a hetero atom, or R$_{725}$ can join with R$_{525}$ to form a 5 to 7 membered heterocyclic ring;
R$_{825}$ is H, C$_{1-10}$ alkyl, arylalkyl, or R$_{425}$ and R$_{825}$ can join together to form a 5 to 7 membered heterocyclic ring;
R$_{925}$ is C$_{1-10}$ alkyl which can join together with R$_{825}$ to form a 5 to 7 membered heterocyclic ring;
each Y is independently —O— or —S(O)$_{0-2}$—;
Z is a bond, —CO—, or —SO$_2$—;
v is 0 to 4; and
each R$_{25}$ present is independently chosen from C$_{1-10}$ alkyl, C$_{1-10}$ alkoxy, hydroxy, halogen and trifluoromethyl;

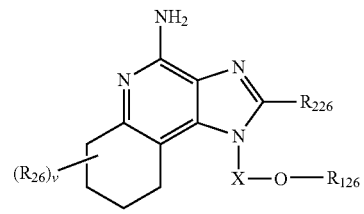

XXVI wherein:
X is —CHR$_{526}$—, —CHR$_{526}$-alkyl-, or —CHR$_{526}$-alkenyl-;
R$_{126}$ is chosen from:
  R$_{426}$—NR$_{826}$—CR$_{326}$—NR$_{526}$-Z-R$_{626}$-alkyl;
  R$_{426}$—NR$_{826}$—CR$_{326}$—NR$_{526}$-Z-R$_{626}$-alkenyl;
  R$_{426}$—NR$_{826}$—CR$_{326}$—NR$_{526}$-Z-R$_{626}$-aryl;
  R$_{426}$—NR$_{826}$—CR$_{326}$—NR$_{526}$-Z-R$_{626}$-heteroaryl;
  R$_{426}$—NR$_{826}$—CR$_{326}$—NR$_{526}$-Z-R$_{626}$-heterocyclyl;
  R$_{426}$—NR$_{826}$—CR$_{326}$—NR$_{526}$R$_{726}$;
  R$_{426}$—NR$_{826}$—CR$_{326}$—NR$_{926}$-Z-R$_{626}$-alkyl;
  R$_{426}$—NR$_{826}$—CR$_{326}$—NR$_{926}$-Z-R$_{626}$-alkenyl;
  R$_{426}$—NR$_{826}$—CR$_{326}$—NR$_{926}$-Z-R$_{626}$-aryl;
  R$_{426}$—NR$_{826}$—CR$_{326}$—NR$_{926}$-Z-R$_{626}$-heteroaryl; and
  R$_{426}$—NR$_{826}$—CR$_{326}$—NR$_{926}$-Z-R$_{626}$-heterocyclyl;
R$_{226}$ is chosen from:
  hydrogen;
  alkyl;
  alkenyl;
  aryl;
  heteroaryl;
  heterocyclyl;
  alkyl-Y-alkyl;
  alkyl-Y-alkenyl;
  alkyl-Y-aryl; and
  alkyl or alkenyl substituted by one or more substituents chosen from:
    OH;
    halogen;
    N(R$_{526}$)$_2$;
    CO—N(R$_{526}$)$_2$;
    CO—C$_{1-10}$ alkyl;
    CO—O—C$_{1-10}$ alkyl;
    N$_3$;
    aryl;
    heteroaryl;
    heterocyclyl;
    CO-aryl; and
    CO-heteroaryl;
each R$_{326}$ is =O or =S;
each R$_{426}$ is independently alkyl or alkenyl, which may be interrupted by one or more —O— groups;
each R$_{526}$ is independently H or C$_{1-10}$ alkyl;
R$_{626}$ is a bond, alkyl, or alkenyl, which may be interrupted by one or more —O— groups;
R$_{726}$ is H, C$_{1-10}$ alkyl which may be interrupted by a hetero atom, or R$_{726}$ can join with R$_{526}$ to form a 5 to 7 membered heterocyclic ring;
R$_{826}$ is H, C$_{1-10}$ alkyl, arylalkyl, or R$_{426}$ and R$_{826}$ can join together to form a 5 to 7 membered heterocyclic ring;
R$_{926}$ is C$_{1-10}$ alkyl which can join together with R$_{826}$ to form a 5 to 7 membered heterocyclic ring;
each Y is independently —O— or —S(O)$_{0-2}$—;

Z is a bond, —CO—, or —SO$_2$—;
v is 0 to 4; and
each R$_{26}$ present is independently chosen from C$_{1-10}$ alkyl, C$_{1-10}$ alkoxy, hydroxy, halogen, and trifluoromethyl;
and pharmaceutically acceptable salts of any of the foregoing.

In another embodiment, the IRM compound can be chosen from 1H-imidazo[4,5-c]pyridin-4-amines compounds defined by Formula XXVII

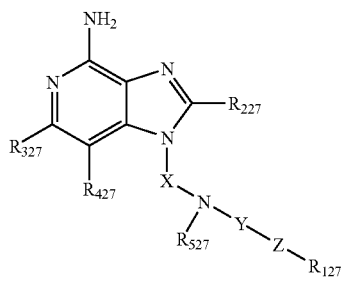

XXVII wherein
X is alkylene or alkenylene;
Y is —CO—, —CS—, or —SO$_2$—;
Z is a bond, —O—, —S—, or —NR$_{527}$—;
R$_{127}$ is aryl, heteroaryl, heterocyclyl, C$_{1-20}$ alkyl or C$_{2-20}$ alkenyl, each of which may be unsubstituted or substituted by one or more substituents independently chosen from:
  alkyl;
  alkenyl;
  aryl;
  heteroaryl;
  heterocyclyl;
  substituted cycloalkyl;
  O-alkyl;
  O-(alkyl)$_{0-1}$-aryl;
  O-(alkyl)$_{0-1}$heteroaryl;
  O-(alkyl)$_{0-1}$-heterocyclyl;
  COOH;
  CO—O-alkyl;
  CO-alkyl;
  S(O)$_{0-2}$-alkyl;
  S(O)$_{0-2}$-(alkyl)$_{0-1}$aryl;
  S(O)$_{0-2}$-(alkyl)$_{0-1}$heteroaryl;
  S(O)$_{0-2}$-(alkyl)$_{0-1}$heterocyclyl;
  (alkyl)$_{0-1}$N(R$_{527}$)$_2$;
  (alkyl)$_{0-1}$-NR$_{527}$—CO—O-alkyl;
  (alkyl)$_{0-1}$-NR$_{527}$—CO-alkyl;
  (alkyl)$_{0-1}$-NR$_{527}$—CO-aryl;
  (alkyl)$_{0-1}$-NR$_{527}$—CO-heteroaryl;
  N$_3$;
  halogen;
  haloalkyl;
  haloalkoxy;
  CO-haloalkyl;
  CO-haloalkoxy;
  NO$_2$;
  CN;
  OH;
  SH; and in the case of alkyl, alkenyl, and heterocyclyl, oxo;
R$_{227}$ is chosen from:
  hydrogen;
  alkyl;
  alkenyl;
  alkyl-O-alkyl;
  alkyl-S-alkyl;
  alkyl-O-aryl;
  alkyl-S-aryl:
  alkyl-O-alkenyl;
  alkyl-S— alkenyl; and
  alkyl or alkenyl substituted by one or more substituents chosen from:
    OH;
    halogen;
    N(R$_{527}$)$_2$;
    CO—N(R$_{527}$)$_2$;
    CS—N(R$_{527}$)$_2$;
    SO$_2$—N(R$_{527}$)$_2$;
    NR$_{527}$—CO—C$_{1-10}$ alkyl;
    NR$_{527}$—CS—C$_{1-10}$ alkyl;
    NR$_{527}$—SO$_2$—C$_{1-10}$ alkyl;
    CO—C$_{1-10}$ alkyl;
    CO—O—C$_{1-10}$ alkyl;
    N$_3$;
    aryl;
    heteroaryl;
    heterocyclyl;
    CO-aryl; and
    CO-heteroaryl;
R$_{327}$ and R$_{427}$ are independently chosen from hydrogen, alkyl, alkenyl, halogen, alkoxy, amino, alkylamino, dialkylamino and alkylthio;
each R$_{527}$ is independently H or C$_{1-10}$alkyl;
and pharmaceutically acceptable salts thereof.

As used herein, the terms "alkyl", "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl and adamantyl.

The term "haloalkyl" is inclusive of groups that are substituted by one or more halogen atoms, including perfluorinated groups. This is also true of groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

"Heterocyclyl" includes non-aromatic rings or ring systems that contain at least one ring hetero atom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, and the like.

In some embodiments, the topical formulations of the present invention are prepared using the free base form of the IRM compound.

The amount of an IRM compound that will be therapeutically effective in a specific situation will depend on such things as the activity of the particular compound, the dosing regimen, the application site, the particular formulation and the condition being treated. As such, it is generally not practical to identify specific administration amounts herein; however, those skilled in the art will be able to determine appropriate therapeutically effective amounts based on the guidance provided herein, information available in the art pertaining to these compounds, and routine testing. The term "a therapeutically effective amount" means an amount of the compound sufficient to induce a therapeutic effect, such as cytokine induction, inhibition of TH2 immune response, antiviral or antitumor activity, reduction or elimination of post-surgical scarring, or reduction or resolution of actinic keratosis or pre-actinic keratosis lesions.

In general, the amount of the IRM compound present in a topical formulation of the invention will be an amount effective to treat a targeted condition, to prevent recurrence of the condition, or to promote immunity against the condition. The amount or concentration of the IRM compound can range from 0.001% to 10% by weight based on the total formulation weight, such as, for example, from 0.03% to 5.0% by weight, or from 0.1 to 1.0% by weight. In certain embodiments, the amount of the IRM compound is at least 0.003% by weight, such as, for example, at least 0.005%, at least 0.01%, at least 0.03%, at least 0.10%, at least 0.30% and at least 1.0%. In other embodiments, the amount of the IRM compound is at most 5.0% by weight, such as, for example, at most 3.0%, and at most 1.0%.

The topical formulations of the invention additionally comprise a fatty acid. As used herein, the term "fatty acid" means a carboxylic acid, either saturated or unsaturated, comprising 6 to 28 carbon atoms, such as, for example, from 10 to 22 carbon atoms. Non-limiting examples of such fatty acids include isostearic acid, oleic acid, and linear- or -branched chained carboxylic acids of 6 to 18 carbon atoms. The fatty acid may be present in the formulation in an amount sufficient to solubilize the IRM compound. In one embodiment, the amount of the fatty acid can range from 0.05% to 40% by weight based on the total weight of the formulation, such as, for example, from 1% to 30%, from 3% to 15% and from 5% to 10%. In certain embodiments, the amount of the fatty acid is at least 3.0% by weight, such as, for example, at least 5.0%, at least 10.0%, and at least 25%. The fatty acid component of the formulation can comprise one or more fatty acids.

The topical formulations of the invention additionally comprise at least one hydrophobic, aprotic component miscible with the fatty acid and comprising a hydrocarbyl group of 7 or more carbon atoms. By "hydrophobic" is meant that the component is essentially insoluble in water, i.e. immiscible with water and unable to form a micelle in water, and does not contain polyoxyethylene or acid salt groups. Preferably the hydrophobic, aprotic component has a hydrophilic lipophilic balance (HLB) of less than 2. The HLB of a component may be determined as described, for example, in Attwood, D., Florence, A. T. *Surfactant Systems: Their Chemistry Pharmacy and Biology*. New York: Chapman & Hall, 471-473, 1983. By "aprotic" is meant that the component cannot donate a proton to the IRM and does not contain groups such as carboxyl, hydroxy, primary and secondary amino, primary and secondary amido, or quaternary ammonium groups. Preferably this component has a pKa of at least 14.2 and does not substantially solubilize or form a complex such as an acid-base pair or complex or a hydrogen bond complex with the IRM compound. By "not substantially" is meant that the ratio of the IRM compound's solubility in the hydrophilic, aprotic component to that in isostearic acid is less than 1:40.

Formulations intended for dermal or topical use desirably have a certain minimum amount of an oil phase to provide qualities such as spreadability, feel on the skin, texture, and so on. However, if all the components of the oil phase solubilize the IRM, then the degree of saturation of the IRM in the formulation will decrease, making it more difficult to deliver the IRM from the formulation to the skin. Addition of the hydrophobic, aprotic component can increase the oil phase volume of the topical formulation to provide desirable qualities such as spreadability and feel, while at the same time not appreciably altering the degree of saturation or thermodynamic activity of the IRM. For example, the amount of fatty acid, which solubilizes the IRM, can be reduced to increase the degree of IRM saturation while maintaining a sufficient oil phase volume by virtue of the addition of the hydrophobic, aprotic component, which does not offset the increased IRM saturation. Thus, the topical formulation of the present invention can facilitate both physical property and drug delivery requirements. Degree of saturation and thermodynamic activity of the IRM in these formulations is equal to the IRM concentration in the oil phase divided by the saturation concentration of the IRM in the oil phase. When the topical formulations of the present invention contain saturated IRM the thermodynamic activity or degree of saturation is unity, and when partially saturated the thermodynamic activity or degree of saturation is less than unity.

The amount of the hydrophobic, aprotic component present in a formulation of the invention can range from 1% to 30% by weight based on the total formulation weight, for example, from 3% to 15% by weight, and from 5 to 10% by weight. In certain embodiments, the amount of the hydrophobic, aprotic component is at least 3.0% by weight, for example, at least 5.0%, and at least 10.0%. The weight ratio of the hydrophobic, aprotic component to the fatty acid can be 0.025:1 to 600:1, for example, 0.5:1 to 50:1, and 2:1 to 30:1. The combined amount (weight percent of the total topical formulation weight) of the hydrophobic, aprotic component and the fatty acid can be 2% to 50% by weight, for example 2% to 30%, 5% to 30%, 5% to 20%, and 10% to 20%.

Examples of useful hydrophobic, aprotic components include but are not limited to fatty acid esters, for example, isopropyl mysristate, isopropyl palmitate, diisopropyl dimer dilinoleate; triglycerides, for example, caprylic/capric triglyceride; cetyl esters wax; hydrocarbons of 8 or more carbon atoms, for example, light mineral oil, white petrolatum; and waxes, for example, beeswax. In some embodiments, the hydrophobic, aprotic component is chosen from one or more of isopropyl mysristate, isopropyl palmitate, caprylic/capric triglyceride, and diisopropyl dimer dilinoleate.

The formulations of the present invention can also comprise a hydrophilic viscosity enhancing agent. Examples of suitable hydrophilic viscosity enhancing agents include cellulose ethers such as hydroxypropylmethylcellulose, hydroxyethylcellulose, hydroxypropylcellulose, and carboxymethylcellulose; polysaccharide gums such as xanthan gum; and homopolymers and copolymers of acrylic acid crosslinked with allyl sucrose or allyl pentaerythriol such as those polymers designated as carbomers in the United States Pharmacopoeia. Suitable carbomers include, for example, those available as Carbopol™ 934P, Carbopol 971P, Carbopol 940, Carbopol 974P, Carbopol 980, and Pemulen™ TR-1 (USP/NF Monograph; Carbomer 1342), all available from Noveon, Cleveland, Ohio. In one embodiment of the present invention, the viscosity enhancing agent is chosen from Carbopol 974P and 980. When included, the viscosity enhancing agent is generally present in an amount ranging from 0.1% to 10% by weight of total formulation weight, such as, for example, from 0.5% to 5% by weight, from 0.5% to 1.5% by weight, and from 0.7% to 3% by weight. In certain embodiments, the amount of the viscosity enhancing agent is at least 0.5% by weight, for example, at least 0.6% by weight, at least 0.7% by weight, at least 0.9% by weight, and at least 1.0% by weight.

The formulations of the invention can additionally comprise an emulsifier. Suitable emulsifiers include non-ionic surfactants such as, for example, polysorbate 60, sorbitan monostearate, polyglyceryl-4 oleate, polyoxyethylene(4) lauryl ether, etc. In certain embodiments, the emulsifier is chosen from poloxamers (e.g., Pluronic™ F68, also known as Poloxamer 188, a poly(ethylene glycol)-block-poly(propylene glycol)-block-poly(ethylene glycol), available from BASF, Ludwigshafen, Germany) and sorbitan trioleate (e.g., Span 85 available from Uniqema, New Castle, Del.). If included, the emulsifier is generally present in an amount of 0.1% to 10% by weight of total formulation weight, for example, from 0.5% to 5% by weight, and from 0.75% to 3.5% by weight. In certain embodiments, the amount of the emulsifier is at least 1.0% by weight, for example, at least 2.5%, at least 3.5%, and at least 5.0%.

In certain embodiments of the present invention, the formulation can also include at least one chelating agent. The chelating agent functions to chelate metal ions that may be present in the formulation. Suitable chelating agents include salts of ethylenediaminetetraacetate (EDTA), such as the disodium salt. If included, the chelating agent is generally present in an amount ranging from 0.001% to 0.1% by weight, and preferably from 0.01% to 0.05% by weight. In certain embodiments, the amount of the chelating agent is at least 0.005% by weight, such as, for example, at least 0.01%, and at least 0.05%.

The formulation can also include a preservative system. The preservative system is generally comprised of at least one preservative compound chosen from methylparaben, ethylparaben, propylparaben, phenoxyethanol, iodopropynyl butylcarbamate, sorbic acid, a fatty acid monoester of glycerin such as glycerol monolaurate, and a fatty acid monoester of propylene glycol such as propylene glycol monocaprylate. The preservative system may also include a preservative enhancing solubilizer which enhances the solubility of the preservative in the aqueous phase, examples of which include diethylene glycol monoethyl ether and propylene glycol. In one embodiment, the preservative system can be comprised of methylparaben, propylparaben, and propylene glycol. In another embodiment, the preservative system can be comprised of methylparaben, ethylparaben, and diethylene glycol monoethyl ether. In one embodiment, the preservative system can be comprised of phenoxyethanol, methylparaben or methyl- and ethylparaben, and diethylene glycol monoethyl ether. In another embodiment, the preservative system can be comprised of iodopropynyl butylcarbamate. In another embodiment, the preservative system can be comprised of iodopropynyl butylcarbamate, diethylene glycol monoethyl ether, and poly(ethylene glycol)(4) monolaurate. In another embodiment, the preservative system can be comprised of iodopropynyl butylcarbamate, one or more of methylparaben, ethylparaben, propylparaben, or phenoxyethanol, and diethylene glycol monoethyl ether. In the above embodiments, the methylparaben, ethylparaben, and propylparaben can each be present in the formulations in an amount ranging from 0.01% to 0.5% by weight of the formulation weight, for example, from 0.05% to 0.25% by weight, and from 0.1% to 0.2% by weight. The iodopropynyl butylcarbamate can be present in the formulations in an amount ranging from 0.01% to 0.1%. The phenoxyethanol can be present in the formulations in an amount ranging from 0.1% to 1%. The propylene glycol and diethylene glycol monoethyl ether can each be present in the formulations in an amount ranging from 1% to 30% by weight of the formulation weight, such as, for example, from 5% to 25% by weight, and from 10% to 15% by weight. The preservative system can be present in the formulations in an amount ranging from 0.01% to 30% by weight of the formulation weight, for example, from 0.05% to 30%, from 0.1% to 25% by weight, and from 0.2% to 15% by weight. In a further embodiment, the methylparaben, ethylparaben, propylparaben, iodopropynyl butylcarbamate, and phenoxyethanol can be solubilized in propylene glycol, poly(ethylene glycol)(4) monolaurate, or diethylene glycol monoethyl ether prior to addition to the formulation. The preservative system can be selected such that it meets the criteria for antimicrobial effectiveness set forth in the United States Pharmacopeia <51>.

The formulations of the present invention may additionally comprise at least one pH adjuster. Suitable pH adjusters include organic bases and inorganic bases such as, for example, KOH, NaOH. The pH of the topical formulations of the present invention generally ranges from 3.5 to 7.0. In one embodiment, the pH of the topical formulations of the present invention can range from 4.0 to 6.0, preferably 5.0. In another embodiment of the invention, the pH of the topical formulations of the present invention can range from 5.5 to 6.5, preferably 6.0.

Any of the foregoing formulations can be in the form of an oil-in-water emulsion such as a cream or a lotion. Such an emulsion can comprise an oil phase comprising the IRM compounds, a fatty acid in an amount sufficient to solubilize the IRM compounds, a hydrophobic, aprotic component; and an aqueous phase comprising a hydrophilic viscosity enhancing agent, for example, a carbomer. In certain embodiments, the amount or concentration of the IRM in the oil phase can be at least 0.01%, for example, at least 0.02%, at least 0.1%, and at least 1% with respect to oil phase weight. In other embodiments, the amount or concentration of the IRM in the oil phase can be at most 20%, for example, at most 10%, and at most 5% with respect to oil phase weight. The emulsion can be preserved so that when challenged by an antimicrobial effectiveness test, it meets regulatory requirements for topical creams packaged in multiple-use containers.

Any of the foregoing formulations according to the present invention can be applied to the dermal surfaces of a mammal. Depending on the IRM compound concentration, formulation composition, and dermal surface, the therapeutic effect of the IRM compound may extend only to the superficial layers of the dermal surface or to tissues below the dermal surface. Thus, another aspect of the present invention is directed to a method for the treatment of a dermal associated condition comprising applying to skin one of the foregoing formulations. As used herein, a "dermal associated condition" means an inflammatory, infectious, neoplastic or other condition that involves a dermal surface or that is in sufficient proximity to a dermal surface to be affected by a therapeutic agent topically applied to the dermal surface. Examples of a dermal associated condition include warts, atopic dermatitis, basal cell carcinoma, postsurgical scars, and actinic keratosis.

In one embodiment, the formulations can be applied to the surface of skin for treatment of actinic keratosis (AK). Actinic keratoses are premalignant lesions considered biologically to be either carcinoma in-situ or squamous intraepidermal neoplasia. AK is the most frequent epidermal tumor and is induced by ultraviolet (UV) radiation, typically from sunlight. Because of its precancerous nature, AK may be considered the most important manifestation of sun-induced skin damage.

In some embodiments, the above described formulations are particularly advantageous for dermal application for a period of time sufficient to obtain a desired therapeutic effect without undesired systemic absorption of the IRM.

EXAMPLES

The following Examples are provided to further describe various IRM formulations and methods according to the invention. The examples, however, are not intended to limit the formulations and methods within the spirit and scope of the invention.

Examples 1-7 and Comparative Example C1

Table 1 summarizes topical formulations made in accordance with the present invention in a percentage weight-by-weight basis.

Formulations containing 2-methyl-1-(2-methylpropyl)-1H-imidazo[4,5-c][1,5]naphthyridin-4-amine (IRM Compound 1) were tested for their ability to induce increases in cytokine concentrations in rats following topical application. This study was undertaken to evaluate cytokine induction following a single dosing of various strengths and timepoints or a multiple vs. single dosing of IRM Compound 1. The formulations described above were tested by examining tissue and serum concentrations of TNF-α, MCP-1 (monocyte chemoattractant protein-1) and IFN-α cytokines following drug treatment.

Female CD hairless rats (Charles River Laboratories, Wilmington, Mass.) weighing 200-250 grams were used in all studies. Animals were randomized to treatment groups and dosed five per treatment group.

The rats were acclimated to collars around the neck on two consecutive days prior to actual dosing. The rats were collared before dosing to preventingestion of the drug, and were then dosed topically with 50 μL of active cream or the appropriate placebo on right flank and then housed individually following dosing. At various times following dosing, the rats were anesthetized and blood was collected by cardiac puncture. Blood was allowed to clot at room temperature and serum was separated from the clot via centrifugation and stored at −20° C. until it was analyzed for cytokine concentrations.

TABLE 1

| Ingredient (Compendial Status) | Topical Cream (percentage weight-by-weight) | | | | | | | |
|---|---|---|---|---|---|---|---|---|
| | Comparative Example C1 (Placebo) | Example 1 | Example 2 | Example 3 | Example 4 | Example 5 | Example 6 | Example 7 |
| IRM Compound 1 | 0.00 | 0.001 | 0.003 | 0.010 | 0.03 | 0.10 | 0.30 | 1.00 |
| Isostearic Acid | 5.00 | 5.00 | 5.00 | 5.00 | 5.00 | 5.00 | 7.00 | 10.00 |
| Isopropyl Myristate (NF) | 10.00 | 10.00 | 10.00 | 10.00 | 10.00 | 10.00 | 8.00 | 5.00 |
| Carbomer 974P (NF) | 1.00 | 1.00 | 1.00 | 1.00 | 1.00 | 1.00 | 1.00 | 1.00 |
| Poloxamer 188 (NF) | 2.50 | 2.50 | 2.50 | 2.50 | 2.50 | 2.50 | 2.50 | 2.50 |
| Propylene Glycol (USP) | 15.00 | 15.00 | 15.00 | 15.00 | 15.00 | 15.00 | 15.00 | 15.00 |
| Methylparaben (NF) | 0.20 | 0.20 | 0.20 | 0.20 | 0.20 | 0.20 | 0.20 | 0.20 |
| Propylparaben (NF) | 0.10 | 0.10 | 0.10 | 0.10 | 0.10 | 0.10 | 0.10 | 0.10 |
| Edetate Disodium (USP) | 0.05 | 0.05 | 0.05 | 0.05 | 0.05 | 0.05 | 0.05 | 0.05 |
| Sodium Hydroxide (NF) Solution, 20% w/w | 0.50 | 0.50 | 0.50 | 0.50 | 0.50 | 0.50 | 0.50 | 0.55 |
| Purified Water (USP) | 65.65 | 65.649 | 65.647 | 65.64 | 65.62 | 65.55 | 65.35 | 64.60 |
| Total | 100.00 | 100.00 | 100.00 | 100.00 | 100.00 | 100.00 | 100.00 | 100.00 |

The formulations set forth in Table 1 were prepared in the following manner:

Oil phase preparation: 2-methyl-1-(2-methylpropyl)-1H-imidazo[4,5-c][1,5]naphthyridin-4-amine (IRM compound 1) was dissolved in isostearic acid and isopropyl myristate, with heat if necessary. Carbomer 974P was then dispersed in the oil phase.

Water phase preparation: Edetate disodium was dissolved in the water. Methylparaben and propylparaben were dissolved in propylene glycol and the solution was subsequently added to the water phase. Poloxamer 188 was then added to the water phase and mixed until dissolved.

Phase combination: The oil phase was added to the water phase at ambient conditions. The emulsion was then homogenized. After homogenization, sodium hydroxide solution (20% w/w) was added and the resulting cream was mixed until smooth and uniform. The pH of the cream was measured and a pH adjustment was made with additional sodium hydroxide solution, if necessary, to meet the in-process target pH of 5.

Following blood collection, the rats were euthanized and their skins removed. Tissue from both treated site (at) and contralateral site (away) were obtained using an 8 mm punch biopsy, weighed, placed in a sealed 1.8 ml cryovial and flash frozen in liquid nitrogen. The frozen tissue sample was then suspended in 1.0 mL RPMI medium (Celox, Hopkins, Minn.) containing 10% fetal bovine serum (Sigma, St. Louis, Mo.), 2 mM L-glutamine, penicillin/streptomycin, and 2-mercaptoethanol (RPMI complete) combined with a protease inhibitor cocktail set III (Calbiochem, San Diego, Calif.). The tissue was homogenized using a Tissue Tearor™ (Biospec Products, Bartlesville, Okla.) for approximately 1 minute. The tissue suspension was then centrifuged at 2000 rpm for 10 minutes under refrigeration to pellet debris, and the supernatant collected and stored at −20° C. until analyzed for cytokine concentrations.

ELISAs for rat MCP-1 were purchased from BioSource Intl. (Camarillo, Calif.) and rat TNF-α were purchased from BD Pharmingen (San Diego, Calif.) and performed according to manufacturer's specifications. Results for both TNF-α, and MCP-1 were expressed in pg/200 mg tissue or pg/ml serum. The sensitivity of the TNF-α ELISA was 31.2 pg/ml and of the MCP-1 ELISA was 11.7 pg/ml. IFN-α concentrations in both serum and skin tissue were determined using a bioassay that measured inhibition of the viral cytopathic effect of vesicular stomatitis virus on rat LMS-C2 fibroblast cells as previously described (Reiter, M. J., Testerman, T. L., Miller, R. L., Weeks, C. E., and Tomai, M. A. (1994) "Cytokine Induction in Mice by the Immunomodulator Imiquimod." J. Leukocyte Biol. 55, 234-240). IIT Research Institute, Chicago Ill., performed these assays. Results for IFN-α concentrations were normalized to a standard reference rat IFN-α, preparation with results being reported in U/mL and are normalized per mg of tissue.

The data shown below in Tables 2-4 are from three separate experiments and analyzed to 1) measure pharmacokinetics by full time course, 2) measure dose response and 3) measure multiple vs. single dosing.

In order to determine the kinetics of local and systemic cytokine production following local administration of IRM Compound 1, the full time course study (Study 1 with results in Table 2) was done by topically dosing rats with the topical cream formulation of Example 7. Serum and tissue samples were taken at 1, 2, 4, 8, 16, 24 and 48 hours post dose. Multiple cytokines (MCP-1, TNF-α and IFN-α) were analyzed separately.

With the tissue data, for each hour measured, a paired t-test (used to eliminate within subject variability) analyzed the difference between treated tissue and control tissue from the same animal. A p-value less than alpha=0.05 indicated a statistically significant difference between the treated and control tissue at that hour. The data are presented in Table 2.

TABLE 2

Cytokine Concentrations in Rat Serum and Dermal Tissue Following Application of the Topical Formulation of Example 7 Full Time Course[a]

| Time (hours) | | Cytokine Concentration[b] | | |
|---|---|---|---|---|
| Post Dose | Dose | Serum | Treated Site | Control site |
| | | TNF-α | | |
| 0 | untreated | 0 | NA | 96 ± 5 |
| 16 | placebo | 0 | 103 ± 8 | 71 ± 6 |
| 1 | 1% | 6 ± 6 | 318 ± 33[c] | 96 ± 13 |
| 2 | 1% | 0 | 1125 ± 74[c] | 124 ± 18 |
| 4 | 1% | 0 | 1120 ± 51[c] | 129 ± 11 |
| 8 | 1% | 24 ± 16 | 429 ± 56[c] | 91 ± 12 |
| 16 | 1% | 6 ± 4 | 231 ± 22[c] | 87 ± 27 |
| 24 | 1% | 32 ± 32 | 198 ± 28[c] | 103 ± 13 |
| 48 | 1% | 49 ± 49 | 74 ± 10 | 69 ± 15 |
| | | MCP-1 | | |
| 0 | untreated | 81 ± 30 | NA | 44 ± 2 |
| 16 | placebo | 144 ± 9 | 144 ± 41 | 42 ± 3 |
| 1 | 1% | 86 ± 29 | 40 ± 8 | 42 ± 3 |
| 2 | 1% | 123 ± 31 | 234 ± 29[c] | 50 ± 4 |
| 4 | 1% | 101 ± 28 | 723 ± 89[c] | 41 ± 5 |
| 8 | 1% | 438 ± 91[c] | 1474 ± 202[c] | 38 ± 3 |
| 16 | 1% | 424 ± 96[c] | 1209 ± 325[c] | 31 ± 5 |
| 24 | 1% | 187 ± 39 | 813 ± 151[c] | 39 ± 1 |
| 48 | 1% | 141 ± 24 | 145 ± 48[c] | 36 ± 6 |
| | | IFN-α | | |
| 0 | untreated | <200 | NA | <650 |
| 16 | placebo | <200 | <650 | <650 |
| 1 | 1% | <200 | <650 | <650 |
| 2 | 1% | <200 | <650 | <650 |
| 4 | 1% | <200 | <650 | <650 |
| 8 | 1% | <200 | 3/5 ≧ 650 | <650 |

TABLE 2-continued

Cytokine Concentrations in Rat Serum and Dermal Tissue Following Application of the Topical Formulation of Example 7 Full Time Course[a]

| Time (hours) | | Cytokine Concentration[b] | | |
|---|---|---|---|---|
| Post Dose | Dose | Serum | Treated Site | Control site |
| 16 | 1% | <200 | <650 | <650 |
| 24 | 1% | <200 | <650 | <650 |
| 48 | 1% | <200 | <650 | <650 |

[a]Female hairless CD rats were dosed topically with cream formulated Compound 1.
[b]TNF-α and MCP-1 were measured by ELISA. IFN-α was measured by bioassay. Results are presented in pg/ml for serum samples and pg/200 mg tissue for tissue samples and represent the mean of five animals ± SEM.
[c]Indicates p < 0.05 when compared to either placebo for serum samples or the difference between treated tissue and control tissue from the same animal.

A multiple dose study was done to monitor effects of a multiple dose regimen (Study 2 with results shown in Table 3). Rats were dosed two times a week for six hours for three weeks with topical cream formulation of Example 5. Placebo (Comparative Example C1) and single dosed rats were done for comparison and done simultaneously with the last dosing of the multiple dose set. Serum and tissue samples were taken at 8 and 24 hours post dose and analyzed for MCP-1.

An analysis identical to that of Study 1 was performed for Study 2. This data set was broken up by treatment (multiple- or single-use) and time point prior to analysis. Again, placebo data were recorded only at the 8-hour time point for single use, but were used to compare placebo to every treatment and time point combination separately. The results are set forth in Table 3 below.

TABLE 3

Cytokine Concentrations in Rat Serum and Dermal Tissue Following Topical Application of the Topical Cream Formulation of Example 5 Multiple vs. Single Dose[a]

| Time (hours) | | Cytokine Concentration[b] MCP-1 | | |
|---|---|---|---|---|
| Post Dose | Dose | Serum | Treated Site | Control Site |
| 0 | None (untreated) | 89 ± 11 | NA | 20 ± 10 |
| 24 | Placebo | 41 ± 14 | 42 ± 15 | 28 ± 6 |
| 8 | Multiple 0.1% | 71 ± 13 | 784 ± 48[c] | 42 ± 5 |
| 24 | Multiple 0.1% | 105 ± 36 | 145 ± 23[c] | 32 ± 6 |
| 8 | Single 0.1% | 73 ± 9 | 519 ± 99[c] | 33 ± 6 |
| 24 | Single 0.1% | 82 ± 3[c] | 412 ± 130[c] | 35 ± 7 |

[a]Female hairless CD rats were dosed topically with cream formulated Compound 1.
[b]MCP-1 was measured by ELISA. Results are presented in pg/ml for serum samples and pg/200 mg tissue for tissue samples and represent the mean of five animals ± SEM.
[c]Indicates p < 0.05 when compared to either placebo for serum samples or the difference between treated tissue and control tissue from the same animal.

A dose response study (Study 3 with results shown in Table 4) was performed by dosing with the topical cream formulations of Examples 3-5 and 7, containing various concentrations of IRM Compound 1. Serum and tissue samples were taken at 8 and 24 hours post dose and analyzed for MCP-1. The studies tested topical delivery of creams comprising IRM Compound 1 for its ability to affect a local MCP-1 induction at four concentrations.

Serum data compared active treatment to placebo (Comparative Example C1) separately at each specified time point. Note that the placebo group was only measured at 24 hours post dose and these observations were compared to each time point for the active group.

TABLE 4

Cytokine Concentrations in Rat Serum and Dermal Tissue Following Topical Application of the Formulations of Examples 3-5 and 7[a]

| Time (hours) Post Dose | Dose | Cytokine Concentration[b] MCP-1 | | |
|---|---|---|---|---|
| | | Serum | Treated Site | Control Site |
| 0 | controls | 207 ± 96 | NA | 38 ± 12 |
| 24 | placebo (Comparative Example C1) | 367 ± 178 | 61 ± 14 | 20 ± 5 |
| 8 | 0.01% (Example 3) | 81 ± 23 | 61 ± 12 | 36 ± 7 |
| 8 | 0.03% (Example 4) | 81 ± 20 | 271 ± 29 | 48 ± 5 |
| 8 | 0.1% (Example 5) | 153 ± 14 | 1119 ± 122[c] | 51 ± 8 |
| 8 | 1.0% (Example 7) | 136 ± 23 | 1370 ± 99[c] | 50 ± 15 |
| 24 | 0.01% (Example 3) | 71 ± 18 | 183 ± 49[c] | 33 ± 13 |
| 24 | 0.03% (Example 4) | 71 ± 20 | 212 ± 49[c] | 40 ± 7 |
| 24 | 0.1% (Example 5) | 226 ± 73 | 628 ± 127[c] | 40 ± 11 |
| 24 | 1.0% (Example 7) | 149 ± 45 | 756 ± 38[c] | 30 ± 9 |

[a]Female hairless CD rats were dosed topically with cream formulated Compound 1.
[b]MCP-1 was measured by ELISA. Results are presented in pg/ml for serum samples and pg/200 mg tissue for tissue samples and represent the mean of five animals ± SEM.
[c]Indicates p < 0.05 when compared to either placebo for serum samples or the difference between treated tissue and control tissue from the same animal.

Examples 8-13

Table 5 summarizes topical formulations made in accordance with the present invention in a percentage weight-by-weight basis.

TABLE 5

| Ingredient (Compendial Status) | Topical Cream (percentage weight-by-weight) | | | | | |
|---|---|---|---|---|---|---|
| | Example 8 | Example 9 | Example 10 | Example 11 | Example 12 | Example 13 |
| IRM Compound 2 | 0.01 | 0.03 | 0.10 | 1.00 | 0.003 | 0.30 |
| Isostearic Acid | 5.00 | 5.00 | 5.00 | 10.00 | 5.00 | 5.00 |
| Isopropyl Myristate (NF) | 10.00 | 10.00 | 10.00 | 5.00 | 10.00 | 10.00 |
| Carbomer 974P (NF) | 1.00 | 1.00 | 1.00 | 0.75 | 1.00 | 1.00 |
| Poloxamer 188 (NF) | 2.50 | 2.50 | 2.50 | 2.50 | 2.50 | 2.50 |
| Propylene Glycol (USP) | 15.00 | 15.00 | 15.00 | 15.00 | 15.00 | 15.00 |
| Methylparaben (NF) | 0.20 | 0.20 | 0.20 | 0.20 | 0.20 | 0.20 |
| Propylparaben (NF) | 0.10 | 0.10 | 0.10 | 0.10 | 0.10 | 0.10 |
| Edetate Disodium (USP) | 0.05 | 0.05 | 0.05 | 0.05 | 0.05 | 0.05 |
| Sodium Hydroxide (NF) Solution, 20% w/w | 0.50 | 0.50 | 0.50 | 0.35 | 0.50 | 0.50 |
| Purified Water (USP) | 65.64 | 65.62 | 65.55 | 65.05 | 65.647 | 65.35 |
| Total | 100.00 | 100.00 | 100.00 | 100.00 | 100.00 | 100.00 |

The formulations set forth in Table 5 were prepared in the following manner:

Oil phase preparation: N-[4-(4-Amino-2-butyl-1H-imidazo[4,5-c][1,5]naphthyridin-1-yl)butyl]-N'-cyclohexylurea (IRM Compound 2) was dissolved in isostearic acid and isopropyl myristate, with heat if necessary. Carbomer 974P was then dispersed in the oil phase.

Water phase preparation: Edetate disodium was dissolved in the water. Methylparaben and propylparaben were dissolved in propylene glycol, and the solution was subsequently added to the water phase. Poloxamer 188 was then added to the water phase and mixed until dissolved.

Phase combination: The oil phase was added to the water phase at ambient conditions. The emulsion was then homogenized. After homogenization, sodium hydroxide solution (20% w/w) was added and the resulting cream was mixed until smooth and uniform. The pH of the cream was measured, and a pH adjustment was made with additional sodium hydroxide solution, if necessary, to meet the in-process target pH of 5.

Formulations containing N-[4-(4-Amino-2-butyl-1H-imidazo[4,5-c][1,5]naphthyridin-1-yl)butyl]-N'-cyclohexylurea (IRM Compound 2) were tested for their ability to induce increases in cytokine concentrations in rats following topical application. This study was undertaken to evaluate cytokine induction following a single dosing of various strengths and timepoints or a multiple vs. single dosing of IRM Compound 2. The formulations described above were tested by examining tissue and serum concentrations of TNF-α, MCP-1 and IFN-α following drug treatment as described in Examples 1-7.

The data shown below in Tables 6-8 are from three separate experiments and analyzed to 1) measure pharmacokinetics by full time course, 2) measure dose response and 3) measure multiple vs. single dosing.

In order to determine the kinetics of local and systemic cytokine production following local administration of IRM Compound 2, the full time course study (Study 1 with results in Table 6) was done by topically dosing rats with the topical cream formulation of Example 11 as described in Examples 1-7. The data are presented in Table 6.

TABLE 6

Cytokine Concentrations in Rat Serum and Dermal Tissue Following Application of the Topical Formulation of Example 11 Full Time Course[a]

| Time (hours) Post Dose | Dose | Cytokine Concentration[b] | | |
|---|---|---|---|---|
| | | Serum | Treated Site | Control site |
| | | TNF-α | | |
| 0 | untreated | 29 ± 15 | NA | 70 ± 11 |
| 16 | placebo | 42 ± 9 | 131 ± 32 | 69 ± 11 |

TABLE 6-continued

Cytokine Concentrations in Rat Serum and Dermal Tissue Following Application of the Topical Formulation of Example 11 Full Time Course[a]

| Time (hours) | | Cytokine Concentration[b] | | |
|---|---|---|---|---|
| Post Dose | Dose | Serum | Treated Site | Control site |
| 1 | 1% | 38 ± 38 | 44 ± 14 | 35 ± 19 |
| 2 | 1% | 2 ± 2 | 75 ± 20[c] | 33 ± 13 |
| 4 | 1% | 3 ± 3 | 321 ± 18[c] | 62 ± 20 |
| 8 | 1% | 0 | 894 ± 180[c] | 21 ± 9 |
| 16 | 1% | 12 ± 12 | 377 ± 45[c] | 22 ± 12 |
| 24 | 1% | 16 ± 8 | 285 ± 15[c] | 52 ± 14 |
| 48 | 1% | 24 ± 7 | 74 ± 9 | 65 ± 13 |
| | | | MCP-1 | |
| 0 | untreated | 100 ± 20 | NA | 33 ± 7 |
| 16 | placebo | 144 ± 9 | 225 ± 106 | 22 ± 4 |
| 1 | 1% | 117 ± 17 | 56 ± 9 | 55 ± 9 |
| 2 | 1% | 126 ± 29 | 50 ± 13 | 54 ± 8 |
| 4 | 1% | 136 ± 29 | 161 ± 18[c] | 71 ± 9 |
| 8 | 1% | 189 ± 28 | 1020 ± 319 | 45 ± 15 |
| 16 | 1% | 297 ± 35 | 1294 ± 122[c] | 40 ± 9 |
| 24 | 1% | 217 ± 12 | 1044 ± 185[c] | 41 ± 11 |
| 48 | 1% | 120 ± 22 | 134 ± 14[c] | 34 ± 7 |
| | | | IFN-α | |
| 0 | untreated | <65 | NA | <650 |
| 16 | placebo | <65 | <650 | <650 |
| 1 | 1% | <65 | <650 | <650 |
| 2 | 1% | <65 | <650 | <650 |
| 4 | 1% | <65 | <650 | <650 |
| 8 | 1% | <65 | 901 ± 571 | <650 |
| 16 | 1% | <65 | 1330 ± 386[c] | <650 |
| 24 | 1% | <65 | <650 | <650 |
| 48 | 1% | <65 | <650 | <650 |

[a]Female hairless CD rats were dosed topically with cream formulated Compound 2.
[b]TNF-α and MCP-1 were measured by ELISA. IFN-α was measured by bioassay. Results are presented in pg/ml for serum samples and pg/200 mg tissue for tissue samples and represent the mean of five animals ± SEM.
[c]Indicates p < 0.05 when compared to either placebo for serum samples or the difference between treated tissue and control tissue from the same animal.

A multiple dose study was done to monitor effects of a multiple dose regimen (Study 2 with results shown in Table 7). Rats were dosed two times a week for six hours for three weeks with topical cream formulation of Example 10. Placebo (Comparative Example C1) and single dosed rats were done for comparison and done simultaneously with the last dosing of the multiple dose set. Serum and tissue samples were taken at 16 and 24 hours post dose and analyzed for MCP-1.

An analysis identical to that of Study 1 was performed for Study 2. This data set was broken up by treatment (multi or single use) and time point prior to analysis. Again, placebo data were recorded only at the 16-hour time point for single use, but were used to compare placebo to every treatment and time point combination separately. The results are set forth in Table 7 below.

TABLE 7

Cytokine Concentrations in Rat Serum and Dermal Tissue Following Topical Application of the Topical Cream Formulation of Example 10 Multiple vs. Single Dose[a]

| Time (hours) | | Cytokine Concentration[b] MCP-1 | | |
|---|---|---|---|---|
| Post Dose | Dose | Serum | Treated Site | Control Site |
| 0 | None (untreated) | 161 ± 58 | NA | 80 ± 22 |
| 16 | Placebo | 214 ± 35 | 71 ± 16 | 47 ± 11 |
| 16 | Multiple 0.1% | 321 ± 62 | 1173 ± 117[c] | 86 ± 14 |
| 24 | Multiple 0.1% | 217 ± 43 | 388 ± 80[c] | 58 ± 5 |
| 16 | Single 0.1% | 205 ± 32 | 1448 ± 241[c] | 77 ± 15 |
| 24 | Single 0.1% | 279 ± 45 | 1172 ± 288[c] | 90 ± 15 |

[a]Female hairless CD rats were dosed topically with cream formulated Compound 2.
[b]MCP-1 was measured by ELISA. Results are presented in pg/ml for serum samples and pg/200 mg tissue for tissue samples and represent the mean of five animals ± SEM.
[c]Indicates p < 0.05 when compared to either placebo for serum samples or the difference between treated tissue and control tissue from the same animal.

A dose response study (Study 3 with results shown in Table 8) was performed by dosing with the topical cream formulations of Examples 8-11, containing various concentrations of IRM Compound 2. Serum and tissue samples were taken at 16 and 24 hours post dose and analyzed for MCP-1. The studies tested topical delivery of creams comprising IRM Compound 2 for its ability to affect a local MCP-1 induction at four concentrations.

Serum data compared active treatment to placebo (Comparative Example C1) separately at each specified time point. Note that the placebo group was only measured at 16 hours post dose and these observations were compared to each time point for the active group.

TABLE 8

Cytokine Concentrations in Rat Serum and Dermal Tissue Following Topical Application of the Formulations of Examples 8-11[a]

| Time (hours) | | Cytokine Concentration[b] MCP-1 | | |
|---|---|---|---|---|
| Post Dose | Dose | Serum | Treated Site | Control Site |
| 0 | controls | 293 ± 23 | NA | 41 ± 11 |
| 16 | placebo (Comparative Example C1) | 293 ± 76 | 44 ± 10 | 36 ± 12 |
| 16 | 0.01% (Example 8) | 276 ± 50 | 257 ± 85 | 57 ± 20 |
| 16 | 0.03% (Example 9) | 318 ± 86 | 210 ± 10 | 45 ± 9 |
| 16 | 0.10% (Example 10) | 529 ± 141 | 2622 ± 616[c] | 73 ± 9 |
| 16 | 1.0% (Example 11) | 345 ± 51 | 3166 ± 470[c] | 71 ± 11 |
| 24 | 0.01% (Example 8) | 298 ± 65 | 276 ± 87 | 94 ± 32 |
| 24 | 0.03% (Example 9) | 253 ± 34 | 427 ± 238 | 28 ± 14 |
| 24 | 0.10% (Example 10) | 331 ± 93 | 1461 ± 264[c] | 19 ± 7 |
| 24 | 1.0% (Example 11) | 358 ± 52 | 1952 ± 185[c] | 17 ± 6 |

[a]Female hairless CD rats were dosed topically with cream formulated Compound 2.
[b]MCP-1 was measured by ELISA. Results are presented in pg/ml for serum samples and pg/200 mg tissue for tissue samples and represent the mean of five animals ± SEM.
[c]Indicates p < 0.05 when compared to either placebo for serum samples or the difference between treated tissue and control tissue from the same animal.

Examples 14-18

Table 9 summarizes topical formulations made in accordance with the present invention on a percentage weight-by-weight basis.

TABLE 9

| | Topical Creams (percentage weight-by-weight) | | | | |
|---|---|---|---|---|---|
| Ingredients | Ex. 14 | Ex. 15 | Ex. 16 | Ex. 17 | Ex. 18 |
| IRM Compound 1 | 0.01 | 0.10 | 1.00 | 3.00 | 1.00 |
| Isostearic Acid (874) | 5.00 | 5.00 | 10.00 | 25.00 | 10.00 |
| *Diisopropyl dimer dilinoleate | 10.00 | 10.00 | 5.00 | 5.00 | — |
| **Caprylic/capric triglycerides | — | — | — | — | 5.00 |
| Carbomer 980, NF | 0.70 | 0.70 | 0.70 | 0.90 | 0.70 |
| Diethylene glycol monoethyl ether USA - NF | 10.00 | 10.00 | 10.00 | 10.00 | 10.00 |
| Disodium EDTA, USP | 0.05 | 0.05 | 0.05 | 0.05 | 0.05 |
| Poloxamer 188, NF | 2.50 | 2.50 | 2.50 | 2.50 | 2.50 |
| Purified Water | 70.94 | 70.85 | 69.95 | 52.55 | 69.95 |
| Methylparaben, NF | 0.20 | 0.20 | 0.20 | 0.20 | 0.20 |
| Ethylparaben | 0.20 | 0.20 | 0.20 | 0.20 | 0.20 |
| 20% (w/w) NaOH | 0.40 | 0.40 | 0.40 | 0.60 | 0.40 |
| Total % w/w | 100.00 | 100.00 | 100.00 | 100.00 | 100.00 |

*Available under the trade name PRIPURE 3786 from Uniquema, New Castle, DE
**Available under the trade name Crodamol GTCC-PN from Croda, Inc, Parsippany, NJ

Examples 19-24

Table 10 summarizes topical formulations made in accordance with the present invention on a percentage weight-by-weight basis.

TABLE 10

| | Topical Creams (percentage weight-by-weight) | | | | | |
|---|---|---|---|---|---|---|
| Ingredients | Ex. 19 | Ex. 20 | Ex. 21 | Ex. 22 | Ex. 23 | Ex. 24 |
| IRM Compound 2 | 0.003 | 0.03 | 0.10 | 1.00 | 3.00 | 1.00 |
| Isostearic Acid (874) | 5.00 | 5.00 | 5.00 | 10.00 | 25.00 | 10.00 |
| Diisopropyl dimer dilinoleate | 10.00 | 10.00 | 10.00 | 5.00 | 5.00 | — |
| Caprylic/capric triglycerides | — | — | — | — | — | 5.00 |
| Carbomer 980, NF | 0.70 | 0.70 | 0.70 | 0.70 | 0.60 | 0.70 |
| Diethylene glycol monoethyl ether USA - NF | 10.00 | 10.00 | 10.00 | 10.00 | 10.00 | 10.00 |
| Disodium EDTA, USP | 0.05 | 0.05 | 0.05 | 0.05 | 0.05 | 0.05 |
| Poloxamer 188, NF | 2.50 | 2.50 | 2.50 | 2.50 | 2.50 | 2.50 |
| Purified Water | 70.95 | 70.92 | 70.85 | 69.95 | 53.19 | 69.95 |
| Methylparaben, NF | 0.20 | 0.20 | 0.20 | 0.20 | 0.20 | 0.20 |
| Ethylparaben | 0.20 | 0.20 | 0.20 | 0.20 | 0.20 | 0.20 |
| 20% (w/w) NaOH | 0.40 | 0.40 | 0.40 | 0.40 | 0.26 | 0.40 |
| Total % w/w | 100.00 | 100.00 | 100.00 | 100.00 | 100.00 | 100.00 |

The formulations described in Tables 9 and 10 were prepared using the following general method:

Oil Phase Preparation:

The IRM compound was dissolved in isostearic acid and diisopropyl dimer dilinoleate (or caprylic/capric acid triglyceride) with heat if necessary.

Water Phase Preparation:

Edetate disodium was dissolved in the water. Poloxamer 188 was then added to the water phase and mixed until dissolved. Carbomer 980 was then added to the water phase and mixed until the carbomer was fully dispersed and hydrated. Methylparaben and propylparaben were dissolved in diethylene glycol monoethyl ether and the solution was subsequently added to the water phase.

Phase Combination:

The water phase was added to the oil phase at ambient conditions. The emulsion was then mixed at high speed or homogenized. After homogenization, sodium hydroxide solution (20% w/w) was added and the resulting cream was mixed until smooth and uniform. The pH of the cream was measured and a pH adjustment was made with additional sodium hydroxide solution, if necessary, to meet the in-process target pH of 5.

Examples 25-28

Table 11 summarizes topical formulations made in accordance with the present invention on a percentage weight-by-weight basis.

TABLE 11

| | Topical Cream (percentage weight-by-weight) | | | |
|---|---|---|---|---|
| Ingredient | Ex. 25 | Ex. 26 | Ex. 27 | Ex. 28 |
| IRM Compound 1 | 1 | 1 | 1 | 1 |
| Isostearic Acid (874) | 10 | 10 | 10 | 8 |
| Diisopropyl dimer dilinoleate | 5 | 5 | 5 | 1 |
| Carbomer 980, NF | 0.7 | 0.7 | 0.7 | 0.7 |
| Diethylene glycol monoethyl ether USA - NF | 10 | 10 | 10 | 10 |
| Disodium EDTA, USP | 0.05 | 0.05 | 0.05 | 0.05 |
| Poloxamer 188, NF | 2.5 | 2.5 | 2.5 | 2.5 |
| Purified Water | Qs to 100 | Qs to 100 | Qs to 100 | Qs to 100 |
| Methylparaben, NF | 0.2 | 0.2 | 0.2 | 0.2 |
| Ethylparaben | 0.2 | 0.2 | 0.2 | 0.2 |
| 20% (w/w) NaOH | 0.4 | 0.4 | 0.4 | 0.4 |
| 10% iodopropynyl butylcarbamate in PLG-4 laurate | — | 1 | — | — |
| Phenoxyethanol | — | — | 0.5 | — |

Examples 29-135

Topical creams containing the IRM compounds listed in Table 12 were prepared using the general methods described above for Examples 1-24. Each IRM was formulated into one or more of the model formulations shown in Tables 13 and 14. Table 15 summarizes the topical creams that were prepared.

TABLE 12

| IRM Compound | Chemical Name |
|---|---|
| 3 | 1-(2-methylpropyl)-1H-imidazo[4,5-c]quinolin-4-amine |
| 4 | 1-(2-methylpropyl)-1H-imidazo[4,5-c][1,8]naphthyridin-4-amine |
| 5 | 2-butyl-1-(2-methylpropyl)-1H-imidazo[4,5-c][1,8]naphthyridin-4-amine |
| 6 | 1-(2-methylpropyl)-1H-imidazo[4,5-c][1,5]naphthyridin-4-amine |
| 7 | 2-methylthiazolo[4,5-c]quinolin-4-amine |
| 8 | 2-ethoxymethyl-1-phenylmethyl-1H-imidazo[4,5-c][1,5]naphthyridin-4-amine |
| 9 | 2-ethylthiazolo[4,5-c]quinolin-4-amine |
| 10 | 4-amino-2-butyl-α,α-dimethyl-1H-imidazo[4,5-c][1,5]naphthyridine-1-ethanol |
| 11 | $N^1$-[2-(4-amino-1H-imidazo[4,5-c]quinolin-1-yl)ethyl]benzamide |
| 12 | 1-{2-[3-(3-pyridyl)propoxy]ethyl}-1H-imidazo[4,5-c]quinolin-4-amine |
| 13 | 1-(2-phenoxyethyl)-1H-imidazo[4,5-c]quinolin-4-amine |
| 14 | 1-[(R)-1-phenylethyl]-1H-imidazo[4,5-c][1,5]naphthyridin-4-amine |
| 15 | $N^4$-[4-(4-amino-1H-imidazo[4,5-c]quinolin-1-yl)butyl]-4-morpholinecarboxamide |
| 16 | $N^3$-[4-(4-amino-1H-imidazo[4,5-c]quinolin-1-yl)butyl]nicotinamide |
| 17 | 1-{2-[3-(1,3-thiazol-2-yl)propoxy]ethyl}-1H-imidazo[4,5-c]quinolin-4-amine |
| 18 | 1-[2-(pyridin-4-ylmethoxy)ethyl]-1H-imidazo[4,5-c]quinolin-4-amine |
| 19 | 2-methyl-1-[5-(methylsulfonyl)pentyl]-1H-imidazo[4,5-c]quinolin-4-amine |
| 20 | N-[3-(4-amino-2-methyl-1H-imidazo[4,5-c]quinolin-1-yl)propyl]cyclohexanecarboxamide |
| 21 | N-[3-(4-amino-2-methyl-1H-imidazo[4,5-c]quinolin-1-yl)propyl]-2-methylpropanamide |
| 22 | N-[3-(4-amino-2-methyl-1H-imidazo[4,5-c]quinolin-1-yl)propyl]butanamide |
| 23 | 2-butyl-1-{2-[(1-methylethyl)sulfonyl]ethyl}-1H-imidazo[4,5-c]quinolin-4-amine |
| 24 | N-{2-[4-amino-2-(ethoxymethyl)-1H-imidazo[4,5-c]quinolin-1-yl]ethyl}ethanesulfonamide |
| 25 | N-{2-[4-amino-2-(ethoxymethyl)-1H-imidazo[4,5-c]quinolin-1-yl]ethyl}propanamide |
| 26 | 1-[2-(methylsulfonyl)ethyl]-2-propyl-1H-imidazo[4,5-c]quinolin-4-amine |
| 27 | N-{2-[4-amino-2-(ethoxymethyl)-1H-imidazo[4,5-c]quinolin-1-yl]ethyl}-N'-ethylthiourea |
| 28 | 2-ethyl-1-{4-[(1-methylethyl)sulfonyl]butyl}-1H-imidazo[4,5-c]quinolin-4-amine |
| 29 | 2-ethyl-1-[4-(ethylsulfonyl)butyl]-1H-imidazo[4,5-c]quinolin-4-amine |
| 30 | N-{3-[4-amino-2-(ethoxymethyl)-1H-imidazo[4,5-c]quinolin-1-yl]propyl}cyclopentanecarboxamide |
| 31 | N-{3-[4-amino-2-(ethoxymethyl)-6,7-dimethyl-1H-imidazo[4,5-c]pyridin-1-yl]propyl}morpholine-4-carboxamide |
| 32 | 1-(2-methylpropyl)-6,7,8,9-tetrahydro-1H-imidazo[4,5-c]quinolin-4-amine |
| 33 | 8,9,10,11-tetrahydropyrido[1',2':1,2]imidazo[4,5-c]quinolin-6-amine |
| 34 | 4-amino-α,α,2-trimethyl-6,7,8,9-tetrahydro-1H-imidazo[4,5-c]quinoline-1-ethanol |
| 35 | 2-hydroxymethyl-1-(2-methylpropyl)-6,7,8,9-tetrahydro-1H-imidazo[4,5-c]quinolin-4-amine |
| 36 | 2-butyl-1-(2-phenoxyethyl)-1H-imidazo[4,5-c][1,5]naphthyridin-4-amine |
| 37 | N-[3-(4-amino-2-methyl-1H-imidazo[4,5-c]quinolin-1-yl)propyl]methanesulfonamide |

TABLE 13

| | Model Formulation (percentage weight-by-weight) | | | | | | |
|---|---|---|---|---|---|---|---|
| Ingredient | A | B | C | D | E | F | G |
| IRM | 0.01 | 0.1 | 1 | 1 | 1 | 1 | 1 |
| Isostearic acid | 5 | 5 | 5 | 20 | 42 | 13 | 6 |
| Isopropyl myristate | 10 | 10 | 10 | 10 | 2 | 10 | 10 |
| Carbomer 974P | 1 | 1 | 1 | 1 | 1 | 1.5 | 1 |
| Purified water | * | * | * | * | * | * | * |
| Poloxamer 188 | 2.5 | 2.5 | 2.5 | 2.5 | 2.5 | 2.5 | 2.5 |
| Propylene glycol | 15 | 15 | 15 | 15 | 13 | 15 | 15 |
| Xanthan gum | — | — | — | — | 0.4 | — | — |
| Methylparaben | 0.2 | 0.2 | 0.2 | 0.2 | 0.2 | 0.2 | 0.2 |
| Disodium EDTA | 0.05 | 0.05 | 0.05 | 0.05 | 0.05 | 0.05 | 0.05 |
| 20% NaOH | 0.7 | 0.7 | 0.7 | 0.7 | 0.7 | 0.7 | 0.7 |

* Qs to 100

TABLE 14

| | Model Formulation (percentage weight-by-weight) | | | | | |
|---|---|---|---|---|---|---|
| Ingredient | H | I | J | K | L | M |
| IRM | 0.01 | 0.1 | 1 | 1 | 3 | 5 |
| Isostearic acid | 5 | 5 | 5 | 10 | 10 | 10 |
| Diisopropyl dimer dilinoleate | 10 | 10 | 10 | 5 | 5 | 5 |
| Carbomer 980 | 0.7 | 0.7 | 0.7 | 1.0 | 1.0 | 1.0 |
| Purified water | * | * | * | * | * | * |
| Poloxamer 188 | 2.5 | 2.5 | 2.5 | 2.6 | 2.6 | 2.6 |
| Diethylene glycol monoethyl ether | 10 | 10 | 10 | 10 | 10 | 10 |
| Xanthan gum | — | — | — | 0.1 | 0.1 | 0.1 |
| Methylparaben | 0.2 | 0.2 | 0.2 | 0.2 | 0.2 | 0.2 |
| Ethylparaben | 0.2 | 0.2 | 0.2 | 0.2 | 0.2 | 0.2 |
| Disodium EDTA | 0.05 | 0.05 | 0.05 | 0.05 | 0.05 | 0.05 |
| 20% NaOH | 0.4 | 0.4 | 0.4 | 0.4 | 0.4 | 0.4 |

* Qs to 100

TABLE 15

| Example | IRM Compound | Model Formulation |
| --- | --- | --- |
| 29 | 3 | A |
| 30 | 3 | B |
| 31 | 3 | C |
| 32 | 4 | A |
| 33 | 4 | B |
| 34 | 4 | C |
| 35 | 5 | A |
| 36 | 5 | B |
| 37 | 5 | D |
| 38 | 6 | A |
| 39 | 6 | B |
| 40 | 6 | C |
| 41 | 7 | A |
| 42 | 7 | B |
| 43 | 7 | C |
| 44 | 8 | A |
| 45 | 8 | B |
| 46 | 8 | C |
| 47 | 9 | A |
| 48 | 9 | B |
| 49 | 9 | C |
| 50 | 10 | A |
| 51 | 10 | B |
| 52 | 10 | C |
| 53 | 11 | A |
| 54 | 11 | B |
| 55 | 11 | E |
| 56 | 12 | A |
| 57 | 12 | B |
| 58 | 12 | C |
| 59 | 13 | A |
| 60 | 13 | B |
| 61 | 13 | F |
| 62 | 14 | A |
| 63 | 14 | B |
| 64 | 14 | G |
| 65 | 15 | H |
| 66 | 15 | I |
| 67 | 15 | K |
| 68 | 16 | H |
| 69 | 16 | I |
| 70 | 16 | K |
| 71 | 17 | A |
| 72 | 17 | B |
| 73 | 17 | C |
| 74 | 18 | H |
| 75 | 18 | I |
| 76 | 18 | K |
| 77 | 19 | H |
| 78 | 19 | I |
| 79 | 19 | K |
| 80 | 20 | H |
| 81 | 20 | I |
| 82 | 20 | K |
| 83 | 20 | L |
| 84 | 20 | M |
| 85 | 21 | H |
| 86 | 21 | I |
| 87 | 21 | K |
| 88 | 22 | H |
| 89 | 22 | I |
| 90 | 22 | J |
| 91 | 23 | H |
| 92 | 23 | I |
| 93 | 23 | J |
| 94 | 24 | H |
| 95 | 24 | I |
| 96 | 24 | K |
| 97 | 25 | H |
| 98 | 25 | I |
| 99 | 25 | K |
| 100 | 26 | H |
| 101 | 26 | I |
| 102 | 26 | K |
| 103 | 27 | H |
| 104 | 27 | I |
| 105 | 27 | K |
| 106 | 28 | H |
| 107 | 28 | I |
| 108 | 28 | K |
| 109 | 29 | H |
| 110 | 29 | I |
| 111 | 29 | K |
| 112 | 30 | H |
| 113 | 30 | I |
| 114 | 30 | K |
| 115 | 31 | H |
| 116 | 31 | I |
| 117 | 31 | K |
| 118 | 32 | A |
| 119 | 32 | B |
| 120 | 32 | C |
| 121 | 33 | A |
| 122 | 33 | B |
| 123 | 33 | C |
| 124 | 34 | A |
| 125 | 34 | B |
| 126 | 34 | C |
| 127 | 35 | A |
| 128 | 35 | B |
| 129 | 35 | C |
| 130 | 36 | A |
| 131 | 36 | B |
| 132 | 36 | C |
| 133 | 37 | H |
| 134 | 37 | I |
| 135 | 37 | K |

The topical creams of Examples 29-135 were tested using the test method described below. The results are shown in Table 16 below where each value is the mean of the values from the 3 rats in the treatment group.

Single Dose MCP-1 Induction Test Method

Female CD hairless rats (Charles River Laboratories, Wilmington, Mass.) weighing 200-250 grams are used. Animals are randomized to treatment groups and dosed three per treatment group.

The rats are acclimated to collars around the neck on two consecutive days prior to actual dosing. A 50 µL dose of active cream or the appropriate placebo is applied to the right flank and gently rubbed into the skin of the rat. The rats are then collared and housed individually to preventingestion of the drug. At selected post treatment time points, the rats are anesthetized, and blood (3 mls) is collected by cardiac puncture. Blood is allowed to clot at room temperature. Serum is separated from the clot via centrifugation, and stored at −20° C. until it is analyzed for MCP-1 concentration.

Following blood collection, the rats are euthanized, and their skins removed. Tissue samples (4 from each site) from both the treated site and contralateral site (untreated) are obtained using an 8 mm punch biopsy, weighed, placed in a sealed 1.8 ml cryovial, and flash frozen in liquid nitrogen. The frozen tissue sample is then suspended in 1.0 mL RPMI medium (Celox, Hopkins, Minn.) containing 10% fetal bovine serum (Sigma, St. Louis, Mo.), 2 mM L-glutamine, penicillin/streptomycin, and 2-mercaptoethanol (RPMI complete) combined with a protease inhibitor cocktail set III (Calbiochem, San Diego, Calif.). The tissue is homogenized using a Tissue Tearor™ (Biospec Products, Bartlesville, Okla.) for approximately 1 minute. The tissue suspension is then centrifuged at 2000 rpm for 10 minutes under refrigeration to pellet debris, and the supernatant is collected and stored at −20° C. until analyzed for MCP-1 concentration.

ELISAs for rat MCP-1 are purchased from BioSource Intl. (Camarillo, Calif.) and performed according to manufacturer's specifications. Results are expressed in pg/ml, the values for the tissue samples are normalized per 200 mg of tissue. The sensitivity of the MCP-1 ELISA is 12 pg/ml.

TABLE 16

| | MCP-1 (pg/ml) | | | | | | | |
|---|---|---|---|---|---|---|---|---|
| | IRM Cream | | | | | | Placebo Cream | |
| Cream of | 6 hours | | | 24 hours | | | | |
| Example | Serum | Treated | Untreated | Serum | Treated | Untreated | Serum | Untreated |
| 29 | 123 | 202 | 46 | 291 | 55 | 34 | 142 | 59 |
| 30 | 119 | 92 | 31 | 177 | 201 | 43 | 142 | 59 |
| 31 | 212 | 1235 | 54 | 267 | 606 | 125 | 142 | 59 |
| 32 | 26 | 54 | 59 | 79 | 82 | 69 | 54 | 56 |
| 33 | 54 | 70 | 71 | 56 | 74 | 58 | 54 | 56 |
| 34 | 72 | 88 | 58 | 59 | 319 | 69 | 54 | 56 |
| 35 | 170 | 110 | 55 | 162 | 142 | 62 | 80 | 58 |
| 36 | 94 | 674 | 46 | 86 | 1216 | 96 | 80 | 58 |
| 37 | 153 | 1826 | 38 | 136 | 2036 | 77 | 80 | 58 |
| 38 | 178 | 65 | 120 | 211 | 121 | 86 | 142 | 59 |
| 39 | 193 | 220 | 61 | 259 | 263 | 59 | 142 | 59 |
| 40 | 226 | 1204 | 58 | 284 | 1086 | 95 | 142 | 59 |
| 41 | 54 | 82 | 96 | 45 | 88 | 71 | 73 | 96 |
| 42 | 65 | 129 | 78 | 54 | 126 | 88 | 73 | 96 |
| 43 | 77 | 824 | 68 | 89 | 1016 | 93 | 73 | 96 |
| 44 | 86 | 256 | * | 177 | 488 | * | 128 | **28 |
| 45 | 172 | 1444 | * | 157 | 1041 | * | 128 | **28 |
| 46 | 177 | 1720 | * | 406 | 1023 | * | 128 | **28 |
| 47 | 58 | 53 | 59 | 81 | 95 | 73 | 37 | 73 |
| 48 | 71 | 200 | 61 | 63 | 112 | 61 | 37 | 73 |
| 49 | 92 | 1254 | 62 | 83 | 1436 | 75 | 37 | 73 |
| 50 | 170 | 1033 | 56 | * | 655 | 56 | 88 | * |
| 51 | 625 | 551 | 787 | * | 149 | 787 | 88 | * |
| 52 | 811 | 348 | 314 | * | 86 | 314 | 88 | * |
| 53 | 70 | 63 | 46 | 76 | 47 | 45 | 7 | 31 |
| 54 | 68 | 35 | 27 | 71 | 26 | 24 | 7 | 31 |
| 55 | 75 | 35 | 21 | 44 | 33 | 32 | 7 | 31 |
| 56 | 115 | 44 | * | 115 | 425 | * | 201 | **42 |
| 57 | 119 | 411 | * | 267 | 1252 | * | 201 | **42 |
| 58 | 190 | 1560 | * | 476 | 1508 | * | 201 | **42 |
| 59 | 155 | 46 | 36 | 271 | 41 | 53 | 107 | 54 |
| 60 | 123 | 53 | 58 | 175 | 80 | 69 | 107 | 54 |
| 61 | 133 | 172 | 52 | 151 | 1131 | 46 | 107 | 54 |
| 62 | 143 | 211 | 55 | 174 | 428 | 61 | 96 | 26 |
| 63 | 320 | 1614 | 51 | 230 | 1217 | 74 | 96 | 26 |
| 64 | 970 | 1094 | 529 | 425 | 390 | 99 | 96 | 26 |
| 65 | 43 | 34 | 57 | 46 | 81 | 61 | 83 | 59 |
| 66 | 29 | 73 | 28 | 32 | 42 | 74 | 83 | 59 |
| 67 | 19 | 54 | 61 | 25 | 34 | 72 | 83 | 59 |
| 68 | 60 | 77 | 82 | 91 | 72 | 35 | 68 | 72 |
| 69 | 143 | 74 | 52 | 99 | 73 | 59 | 68 | 72 |
| 70 | 59 | 77 | 34 | 91 | 134 | 60 | 68 | 72 |
| 71 | 259 | 79 | 62 | 134 | 84 | 57 | 177 | 53 |
| 72 | 138 | 255 | 65 | 122 | 990 | 63 | 177 | 53 |
| 73 | 251 | 999 | 63 | 293 | 1411 | 108 | 177 | 53 |
| 74 | 99 | 66 | 71 | 73 | 99 | 89 | 61 | 91 |
| 75 | 76 | 101 | 78 | 3 | 170 | 73 | 61 | 91 |
| 76 | 66 | 6779 | 64 | 188 | 4949 | 104 | 61 | 91 |
| 77 | 28 | 47 | 35 | 21 | 43 | 40 | 30 | 38 |
| 78 | 27 | 35 | 37 | 33 | 49 | 59 | 30 | 38 |
| 79 | 24 | 41 | 40 | 27 | 50 | 38 | 30 | 38 |
| 80 | 51 | 59 | 23 | 50 | 163 | 0 | 97 | 15 |
| 81 | 9 | 0 | 15 | 83 | 34 | 10 | 97 | 15 |
| 82*** | 61 | 32 | 0 | 121 | 303 | 45 | 97 | 15 |
| 82*** | 50 | 149 | 36 | 79 | 225 | 76 | 93 | 120 |
| 83 | 110 | 164 | 124 | 61 | 275 | 172 | 93 | 120 |
| 84 | 59 | 177 | 92 | 98 | 629 | 40 | 93 | 120 |
| 85 | 81 | 0 | 0 | 0 | 0 | 0 | 177 | 0 |
| 86 | 116 | 0 | 0 | 0 | 0 | 0 | 177 | 0 |
| 87 | 69 | 0 | 0 | 0 | 0 | 0 | 177 | 0 |
| 88 | 114 | 56 | 41 | 87 | 43 | 42 | 141 | 33 |
| 89 | 74 | 47 | 49 | 132 | 49 | 40 | 141 | 33 |
| 90 | 91 | 96 | 47 | 111 | 109 | 41 | 141 | 33 |
| 91 | 42 | 91 | 53 | 86 | 874 | 57 | 34 | 46 |
| 92 | 83 | 1238 | 74 | 92 | 1087 | 67 | 34 | 46 |
| 93 | 98 | 2037 | 64 | 114 | 1124 | 74 | 34 | 46 |

TABLE 16-continued

| | MCP-1 (pg/ml) | | | | | | | |
|---|---|---|---|---|---|---|---|---|
| | IRM Cream | | | | | | Placebo Cream | |
| Cream of | 6 hours | | | 24 hours | | | | |
| Example | Serum | Treated | Untreated | Serum | Treated | Untreated | Serum | Untreated |
| 94 | 102 | 98 | 107 | 48 | 136 | 133 | 110 | 100 |
| 95 | 49 | 130 | 90 | 95 | 158 | 112 | 110 | 100 |
| 96 | 68 | 255 | 79 | 132 | 528 | 81 | 110 | 100 |
| 97 | 34 | 88 | 106 | 54 | 95 | 92 | 36 | 102 |
| 98 | 17 | 116 | 108 | 83 | 123 | 91 | 36 | 102 |
| 99 | 51 | 150 | 89 | 43 | 945 | 76 | 36 | 102 |
| 100 | 111 | 81 | 83 | 55 | 115 | 72 | 82 | 58 |
| 101 | 33 | 72 | 55 | 75 | 209 | 64 | 82 | 58 |
| 102 | 79 | 489 | 54 | 112 | 3199 | 103 | 82 | 58 |
| 103 | 82 | 88 | 69 | 31 | 107 | 94 | 7 | 61 |
| 104 | 13 | 66 | 55 | 61 | 72 | 63 | 7 | 61 |
| 105 | 75 | 83 | 87 | 54 | 60 | 69 | 7 | 61 |
| 106 | 72 | 96 | 103 | 64 | 168 | 158 | 8 | 137 |
| 107 | 21 | 129 | 98 | 48 | 168 | 75 | 8 | 137 |
| 108 | 95 | 314 | 72 | 135 | 3267 | 128 | 8 | 137 |
| 109 | 72 | 60 | 71 | 71 | 78 | 62 | 12 | 31 |
| 110 | 44 | 76 | 57 | 92 | 72 | 75 | 12 | 31 |
| 111 | 70 | 143 | 83 | 32 | 2397 | 68 | 12 | 31 |
| 112 | 66 | 67 | 120 | 28 | 84 | 70 | 30 | 102 |
| 113 | 46 | 107 | 106 | 70 | 1034 | 93 | 30 | 102 |
| 114 | 14 | 627 | 65 | 196 | 2880 | 111 | 30 | 102 |
| 115 | 39 | 38 | 41 | 84 | 77 | 90 | 84 | 157 |
| 116 | 73 | 81 | 90 | 64 | 57 | 223 | 84 | 157 |
| 117 | 66 | 113 | 52 | 79 | 91 | 61 | 84 | 157 |
| 118 | 132 | 59 | 59 | 135 | 46 | 52 | * | * |
| 119 | 123 | 184 | 31 | 144 | 104 | 42 | * | * |
| 120 | 124 | 1261 | 45 | 171 | 892 | 56 | * | * |
| 121 | 90 | 74 | 51 | 88 | 96 | 75 | 78 | 57 |
| 122 | 72 | 415 | 50 | 91 | 613 | 82 | 78 | 57 |
| 123 | 156 | 1502 | 52 | 226 | 1043 | 48 | 78 | 57 |
| 124 | 92 | 94 | 27 | 96 | 95 | 110 | 97 | 652 |
| 125 | 123 | 198 | 128 | 107 | 72 | 120 | 97 | 652 |
| 126 | 136 | 1828 | 97 | 73 | 1348 | 349 | 97 | 652 |
| 127 | 67 | 66 | 46 | 81 | 90 | 22 | 51 | 81 |
| 128 | 63 | 80 | 58 | 55 | 53 | 35 | 51 | 81 |
| 129 | 49 | 382 | 58 | 35 | 809 | 59 | 51 | 81 |
| 130 | 132 | 55 | 41 | 135 | 162 | 43 | 74 | 32 |
| 131 | 124 | 279 | 59 | 144 | 822 | 60 | 74 | 32 |
| 132 | 124 | 1901 | 13 | 171 | 1212 | 11 | 74 | 32 |
| 133 | 64 | 106 | 0 | 52 | 199 | 32 | 26 | 8 |
| 134 | 9 | 76 | 0 | 70 | 59 | 0 | 26 | 8 |
| 135 | 59 | 89 | 0 | 76 | 47 | 0 | 26 | 8 |

\* MCP-1 concentration was not measured

\*\*MCP-1 concentration is for the treated site.

\*\*\*The cream of Example 82 was used in 2 separate experiments

Examples 136-140

Table 17 summarizes topical formulations made in accordance with the present invention on a percentage weight-by-weight basis.

TABLE 17

| | Topical Creams (percentage weight-by-weight) | | | | |
|---|---|---|---|---|---|
| Ingredients | Ex. 136 | Ex. 137 | Ex. 138 | Ex. 139 | Ex. 140 |
| IRM Compound 1 | 1 | 1 | 1 | 1 | 1 |
| Isostearic Acid | 10 | 10 | 8 | 10 | 10 |
| Diisopropyl dimer dilinoleate | — | 5 | 1 | 5 | 5 |
| Caprylic/capric triglycerides | 5 | — | — | — | — |
| Carbomer 980 | 0.7 | 0.7 | 0.7 | 0.7 | 0.7 |
| Diethylene glycol monoethyl ether | 10 | 10 | 10 | 10 | 10 |
| Disodium EDTA | 0.05 | 0.05 | 0.05 | 0.05 | 0.05 |
| Poloxamer 188 | 2.5 | 2.5 | 2.5 | 2.5 | 2.5 |
| Purified Water | Qs to 100 | Qs to 100 | Qs to 100 | Qs to 100 | Qs to 100 |
| Methylparaben | 0.2 | 0.1 | 0.2 | 0.2 | 0.2 |
| Ethylparaben | 0.2 | 0.1 | 0.2 | 0.2 | 0.2 |
| 20% (w/w) NaOH | Qs to pH 5-5.5 | Qs to pH 5-5.5 | Qs to pH 5-5.5 | Qs to pH 6.5 | Qs to pH 5-5.5 |
| Iodopropynyl butylcarbamate | — | 0.1 | — | — | — |
| PEG-4 Laurate | — | 0.9 | — | — | — |
| Phenoxyethanol | — | 1 | — | — | — |
| Sorbic acid | — | 0.15 | — | — | — |

The topical creams of Examples 136-140 were tested using the test method described below. The results are shown in Table 18 below where each value is the mean of the values from the 3 rats in the treatment group. "Normal animals" did not receive any treatment.

Single Dose Cytokine Induction Test Method

Female CD hairless rats (Charles River Laboratories, Wilmington, Mass.) weighing 200-250 grams are used. Animals are randomized to treatment groups and dosed three per treatment group.

The rats are acclimated to collars around the neck on two consecutive days prior to actual dosing. A 50 μL dose of active cream is applied to the right flank and gently rubbed into the skin of the rat. The rats are then collared and housed individually to prevent ingestion of the drug. At 6 hours post treatment, the rats are anesthetized, and blood (3 mls) is collected by cardiac puncture. Blood is allowed to clot at room temperature, serum is separated from the clot via centrifugation, and stored at −20° C. until it is analyzed for cytokine concentrations.

Following blood collection, the rats are euthanized, and their skins removed. Tissue samples (4 from each site) from both the treated site and contralateral site (untreated) are obtained using an 8 mm punch biopsy, weighed, placed in a sealed 1.8 ml cryovial, and flash frozen in liquid nitrogen. The frozen tissue sample is then suspended in 1.0 mL RPMI medium (Celox, Hopkins, Minn.) containing 10% fetal bovine serum (Sigma, St. Louis, Mo.), 2 mM L-glutamine, penicillin/streptomycin, and 2-mercaptoethanol (RPMI complete) combined with a protease inhibitor cocktail set III (Calbiochem, San Diego, Calif.). The tissue is homogenized using a Tissue Tearor™ (Biospec Products, Bartlesville, Okla.) for approximately 1 minute. The tissue suspension is then centrifuged at 2000 rpm for 10 minutes under refrigeration to pellet debris. The supernatant is collected and stored at −20° C. until analyzed for cytokine concentrations.

ELISAs for rat MCP-1 are purchased from BioSource Intl. (Camarillo, Calif.) and rat TNF-α are purchased from BD Pharmingen (San Diego, Calif.) and performed according to manufacturer's specifications. Results are expressed in pg/ml, the values for the tissue samples are normalized per 200 mg of tissue. The sensitivity of the MCP-1 ELISA is 12 pg/ml and the sensitivity of the TNF-α ELISA is 31 pg/ml.

TABLE 18

| | Cytokine Induction | | | | | | | | | |
|---|---|---|---|---|---|---|---|---|---|---|
| | IRM Cream Treated Animals | | | | | | Normal Animals | | | |
| Cream of | MCP-1 (pg/ml) | | | TNF-α (pg/ml) | | | MCP-1 (pg/ml) | | TNF-α (pg/ml) | |
| Example | Serum | Treated | Untreated | Serum | Treated | Untreated | Serum | Tissue | Serum | Tissue |
| 136 | 119 | 1208 | 51 | 64 | 808 | 85 | 73 | 39 | 64 | 67 |
| 137 | 90 | 1815 | 78 | 78 | 597 | 78 | 73 | 39 | 64 | 67 |
| 138 | 5 | 1351 | 27 | 66 | 636 | 69 | 73 | 39 | 64 | 67 |
| 139 | 62 | 1509 | 85 | 50 | 443 | 75 | 73 | 39 | 64 | 67 |
| 140 | 24 | 2373 | 28 | 80 | 948 | 95 | 73 | 39 | 64 | 67 |

What is claimed is:

1. A method of treating a dermal associated condition without undesired systemic absorption of the IRM, the method comprising a step of:
   applying to skin a topical formulation comprising an immune response modifier (IRM) compound 2-methyl-1-(2-methylpropyl)-1H-imidazo[4,5-c][1,5]naphthyridin-4-amine or a pharmaceutically acceptable salt thereof; a fatty acid; and a hydrophobic, aprotic component miscible with the fatty acid and comprising a hydrocarbyl group of 7 or more carbon atoms, wherein the hydrophobic, aprotic component is caprylic/capric triglyceride,
   wherein the formulation is applied for a period of time sufficient to obtain a desired therapeutic effect without undesired systemic absorption of the IRM compound, and the dermal associated condition is selected from the group consisting of actinic keratosis, postsurgical scars, basal cell carcinoma, atopic dermatitis, and warts.

2. The method according to claim 1 wherein the ratio of the hydrophobic, aprotic component to the fatty acid is 0.025:1 to 600:1.

3. The method according to claim 1 wherein the combined weight percent of the hydrophobic, aprotic component and the fatty acid is 2 to 50.

4. The method according to claim 1 wherein the formulation further comprises:
   a preservative system; and
   an emulsifier.

5. The method according to claim 4 wherein the preservative system comprises methylparaben at 0.01 to 0.5% w/w of the formulation and propylparaben at 0.01 to 0.5% w/w of the formulation.

6. The method according to claim 4 wherein the preservative system comprises methylparaben at 0.01 to 0.5% w/w of the formulation and ethylparaben at 0.01 to 0.5% w/w of the formulation.

7. The method according to claim 4 wherein the preservative system comprises iodopropynyl butylcarbamate.

8. The method according to claim 4 wherein the preservative system comprises iodopropynyl butylcarbamate and one or more of methylparaben, ethylparaben, propylparaben, or phenoxyethanol.

9. The method according to claim 4 wherein the preservative system comprises iodopropynyl butylcarbamate, methylparaben, and ethylparaben.

10. The method according to claim 4 wherein the preservative system comprises phenoxyethanol and one or both of methylparaben and ethylparaben.

11. The method according to claim 4 wherein the preservative system comprises a preservative enhancing solubilizer.

12. The method according to claim 11 wherein the preservative enhancing solubilizer comprises diethylene glycol monoethyl ether, propylene glycol or a combination thereof.

* * * * *